US010201272B2

(12) United States Patent
Saito et al.

(10) Patent No.: US 10,201,272 B2
(45) Date of Patent: Feb. 12, 2019

(54) OPHTHALMOLOGIC IMAGING APPARATUS, CONTROL METHOD THEREOF, AND PROGRAM

(71) Applicant: CANON KABUSHIKI KAISHA, Tokyo (JP)

(72) Inventors: Yohei Saito, Kawasaki (JP); Tomoyuki Makihira, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/476,575

(22) Filed: Mar. 31, 2017

(65) Prior Publication Data

US 2017/0290506 A1 Oct. 12, 2017

(30) Foreign Application Priority Data

Apr. 6, 2016 (JP) .................. 2016-076838

(51) Int. Cl.
*A61B 3/10* (2006.01)
*A61B 3/00* (2006.01)
*A61B 3/14* (2006.01)

(52) U.S. Cl.
CPC ............ *A61B 3/102* (2013.01); *A61B 3/0025* (2013.01); *A61B 3/0058* (2013.01); *A61B 3/0075* (2013.01); *A61B 3/14* (2013.01)

(58) Field of Classification Search
CPC ............ A61B 3/14; A61B 3/0025; A61B 3/12; A61B 3/102; A61B 3/0058
USPC ........................................................ 351/206
See application file for complete search history.

(56) References Cited

U.S. PATENT DOCUMENTS

| 2008/0030684 | A1* | 2/2008 | Nawata ................. | A61B 3/102 351/206 |
| 2008/0084538 | A1* | 4/2008 | Maeda ................. | A61B 3/1241 351/206 |
| 2011/0026035 | A1 | 2/2011 | Muto | |
| 2013/0070202 | A1* | 3/2013 | Yonezawa ............ | G06T 7/0012 351/206 |
| 2013/0258286 | A1* | 10/2013 | Iwase ................... | A61B 3/0041 351/208 |

FOREIGN PATENT DOCUMENTS

JP 201591552 A 5/2015

\* cited by examiner

*Primary Examiner* — Mohammed Hasan
(74) *Attorney, Agent, or Firm* — Canon U.S.A., Inc. IP Division

(57) ABSTRACT

An ophthalmologic imaging apparatus which captures a tomographic image of a subject's eye using interference light obtained by combining a return light from the subject's eye irradiated by measurement light and a reference light includes a control unit configured to perform (a) control, when a first imaging mode for capturing the tomographic image of the subject's eye is selected, to display the tomographic image as a first tomographic image of the subject's eye on a display unit and (b) control, when a second imaging mode different from the first imaging mode is selected, to display a second tomographic image of the subject's eye on the display unit, the second tomographic image generated using the tomographic image to increase intensity of the second tomographic image higher than that of the first tomographic image.

16 Claims, 12 Drawing Sheets

310

320

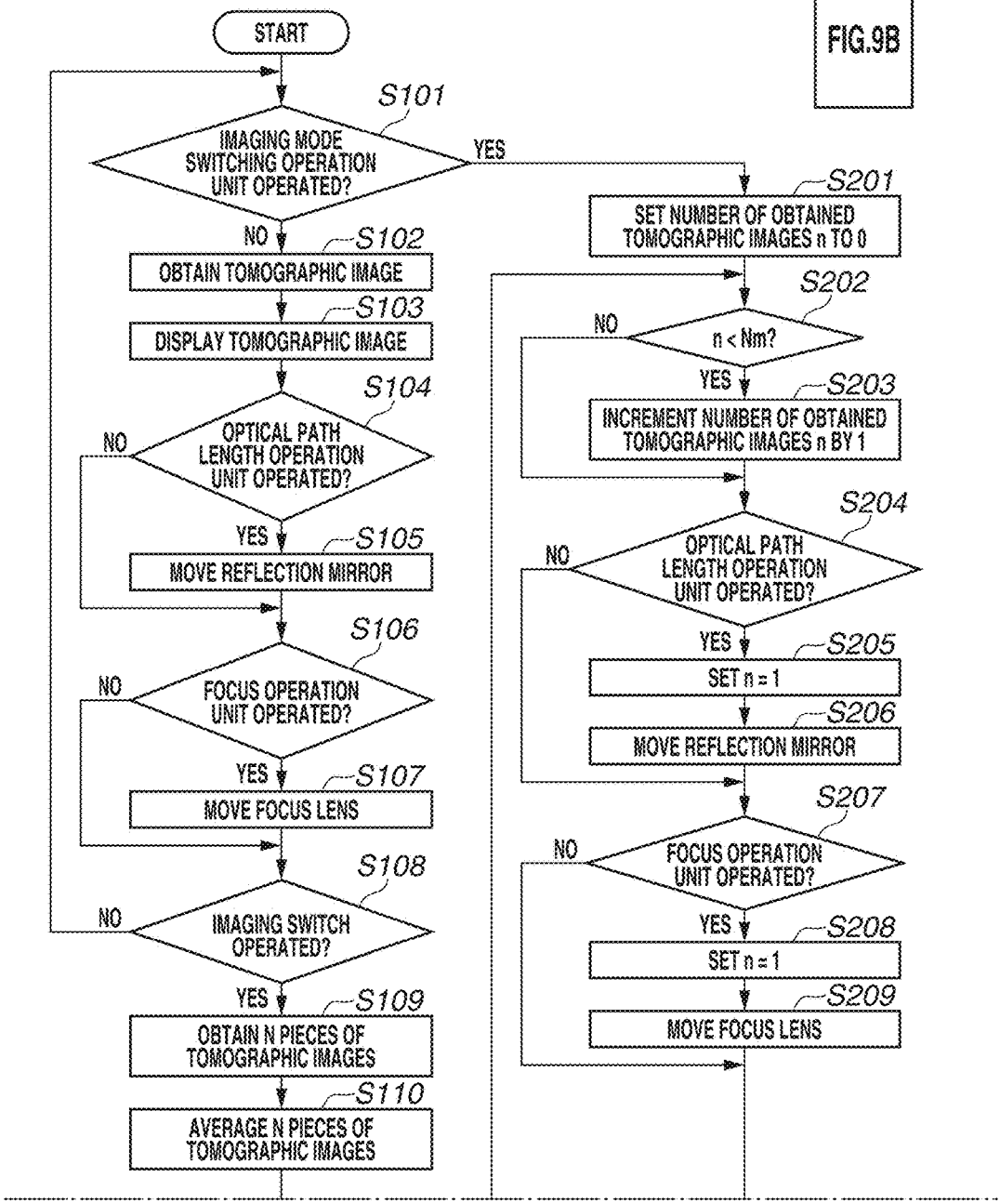

OPHTHALMOLOGIC IMAGING APPARATUS, CONTROL METHOD THEREOF, AND PROGRAM

BACKGROUND OF THE INVENTION

Field of the Invention

The present invention relates to an ophthalmologic imaging apparatus for capturing a tomographic image of a subject's eye, a control method thereof, and a program for causing a computer to execute the control method of the ophthalmologic imaging apparatus.

Description of the Related Art

Currently, application fields of optical interference tomograph meters of optical coherence tomography (OCT) utilizing multi-wavelength light wave interference are spread with respect to human bodies to obtain, for example, information of internal organs by endoscopes and information of retinas of eyes by ophthalmologic imaging apparatuses. Apparatuses of the optical interference tomograph meters applicable to eyes are becoming essential apparatuses as the ophthalmologic imaging apparatuses in specialized outpatient cares for retina.

The apparatuses of the optical interference tomograph meters can illuminate samples with measurement light which is low coherent light and measure return light of the measurement light from the samples using interference systems. In the case of the ophthalmologic imaging apparatuses which are the apparatuses of the optical interference tomograph meters applicable to eyes, the apparatuses can capture tomographic images of subject's eyes at high resolution by scanning the measurement light on the subject's eyes and thus are widely used in ophthalmic diagnoses of retina and the like. Japanese Patent Application Laid-Open No. 2015-91552 describes an ophthalmologic imaging apparatus which captures a tomographic image of a subject's eye.

SUMMARY OF THE INVENTION

According to an aspect of the present invention, an ophthalmologic imaging apparatus which captures a tomographic image of a subject's eye using interference light obtained by combining a return light from the subject's eye irradiated by measurement light and a reference light, the ophthalmologic imaging apparatus includes a selection unit configured to select any of a plurality of imaging modes including a first imaging mode for capturing the tomographic image of the subject's eye and a second imaging mode which is different from the first imaging mode, and a control unit configured to perform (a) control, in a case that the first imaging mode is selected, to display the tomographic image as a first tomographic image of the subject's eye on a display unit and (b) control, in a case that the second imaging mode is selected, to display a second tomographic image of the subject's eye on the display unit, the second tomographic image generated using the tomographic image so as to increase intensity of the second tomographic image higher than that of the first tomographic image.

According to another aspect of the present invention, a control method of the above-described ophthalmologic imaging apparatus and a program for causing a computer to execute the control method of the ophthalmologic imaging apparatus are provided.

Further features of the present invention will become apparent from the following description of exemplary embodiments with reference to the attached drawings.

DESCRIPTION OF THE EMBODIMENTS

Conventional ophthalmologic imaging apparatuses may not clearly draw tomographic images depending on regions of subject's eyes (for example, vitreous bodies), and it is difficult to observe structures thereof in some cases.

Exemplary embodiments of the present invention are discussed below in consideration of the above-described issues and feature the provision of a mechanism capable of properly observing structures in a plurality of regions of a subject's eye (for example, a retina and a vitreous body).

The exemplary embodiments are described below with reference to the attached drawings.

A first exemplary embodiment of the present invention is first described.

Figure 1:
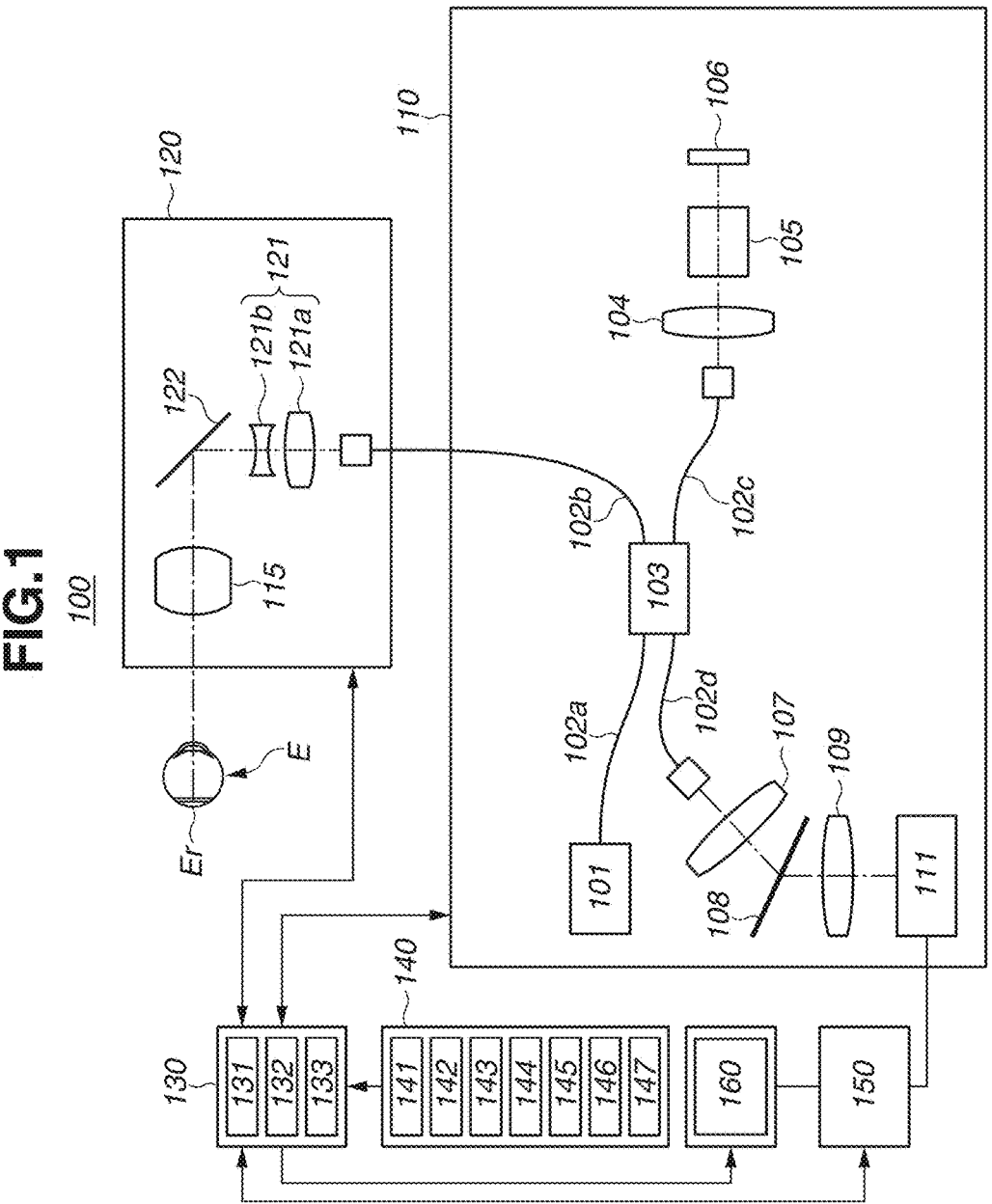
FIG. 1 illustrates an example of a schematic configuration of an ophthalmologic imaging apparatus according to a first exemplary embodiment of the present invention.

FIG. 1 illustrates an example of a schematic configuration of an ophthalmologic imaging apparatus 100 according to the first exemplary embodiment of the present invention. The ophthalmologic imaging apparatus 100 is an apparatus assuming the above-described optical interference tomograph meter.

The ophthalmologic imaging apparatus 100 is an apparatus which captures a tomographic image of a subject's eye E (specifically, a fundus Er of the subject's eye E according to the present exemplary embodiment). The ophthalmologic imaging apparatus 100 includes an optical interference unit 110, a scanning optical unit 120, a control unit 130, an operation unit 140, an image processing unit 150, and a display unit 160 as illustrated in FIG. 1.

The optical interference unit 110 is constituted of a light source 101, optical fibers 102a to 102d, a light branch unit 103, a collimate optical system 104, a dispersion compensation optical system 105, a reflection mirror 106, a lens 107, a diffraction grating 108, an imaging lens 109, and a line sensor 111 as illustrated in FIG. 1.

The scanning optical unit 120 is constituted of an optical system 121 including a collimating lens 121a and a focus lens 121b, a scanning unit 122, and a lens 123 as illustrated in FIG. 1. The control unit 130 is constituted of an optical path length control unit 131, a drive control unit 132, and a focus lens control unit 133 as illustrated in FIG. 1. The operation unit 140 is constituted of an optical path length operation unit 141, an alignment operation unit 142, a focus operation unit 143, an imaging switch 144, a luminance increasing operation unit 145, a luminance decreasing operation unit 146, and an imaging mode switching operation unit 147 as illustrated in FIG. 1.

The light source 101 is a low-coherence light source which outputs, for example, near-infrared light based on control by the control unit 130. The light output from the light source 101 propagates the optical fiber 102a and is branched into measurement light and reference light by the light branch unit 103.

The reference light branched by the light branch unit 103 is introduced into the reflection mirror 106 via the optical fiber 102c. More specifically, the reference light entered to the optical fiber 102c is emitted from a fiber end of the optical fiber 102c, entered to the dispersion compensation optical system 105 via the collimate optical system 104, and introduced into the reflection mirror 106. The dispersion compensation optical system 105 corrects dispersion of the optical system in the scanning optical unit 120 and the subject's eye E which is an object to be measured. The reflection mirror 106 is configured to be movable in an optical axis direction by control of the optical path length control unit 131 in the control unit 130 and is an optical path length adjustment optical unit which adjusts an optical path length of the reference light so as to relatively change with respect to an optical path length of the measurement light. The optical path length control unit 131 in the control unit 130 performs control to place the reflection mirror 106 on a position of a coherence gate at which the optical path length of the measurement light matches with the optical path length of the reference light. The reference light reflected by the reflection mirror 106 passes through the optical path in reverse and enters again in the optical fiber 102c.

The optical path length operation unit 141 is constituted of, for example, a dial with encoder and a sensor and can input to the control unit 130 an amount intended by an examiner by, for example, detecting a rotation amount of the dial by the sensor. Further, the optical path length control unit 131 in the control unit 130 controls the reflection mirror 106 to move by an amount corresponding to an input amount (an operation amount) of the optical path length operation unit 141.

The measurement light branched by the light branch unit 103 is introduced into the scanning optical unit 120 via a fiber end of the optical fiber 102b.

The optical system 121 in the scanning optical unit 120 is constituted of the collimating lens 121a for making the light emitted from the fiber end of the optical fiber 102b approximate parallel light and the focus lens 121b for correcting a difference in a refractive power due to a difference in the subject's eye E. In this regard, the focus lens 121b is configured to be movable in the optical axis direction by control of the focus lens control unit 133 and can correct a refractive error in the subject's eye E. More specifically, the focus lens 121b is a focus adjustment optical unit for adjusting a focus of the measurement light.

The focus operation unit 143 can input an amount intended by an examiner to the control unit 130 by, for example, a configuration similar to that of the optical path length operation unit 141. The focus lens control unit 133 in the control unit 130 controls the focus lens 121b to move by an amount corresponding to an input amount (an operation amount) of the focus operation unit 143.

The scanning unit 122 includes two galvano mirrors which can rotate mirror surfaces. One of the galvano mirror deflects the light in a horizontal direction, and the other galvano mirror deflects the light in a vertical direction, so that the incident light is deflected by control of the drive control unit 132. Accordingly, the scanning unit 122 can perform scanning in two directions, namely a main scanning direction on a sheet surface and a sub-scanning direction which is the vertical direction to the sheet surface. The scanning light from the scanning unit 122 forms a bright spot moving on the subject's eye E (specifically, the fundus Er of the subject's eye E according to the present exemplary embodiment) via the lens 123. The reflected light at a bright spot position passes through the optical path in reverse, enters the optical fiber 102b, and returns to the light branch unit 103.

The alignment operation unit 142 is constituted of a mechanism like, for example, an operation rod. For example, when the alignment operation unit 142 is operated, the drive control unit 132 in the control unit 130 controls the scanning optical unit 120 to relatively move back and forth, up and down, and right and left with respect to the subject's eye E in response to the operation.

As described above, the reference light reflected by the reflection mirror 106 and the measurement light reflected by the subject's eye E are returned to the light branch unit 103 as return light and cause light interference. The interference light interfered with each other passes through the optical fiber 102d, is approximately parallelized by being emitted from the lens 107, and enters the diffraction grating 108. The diffraction grating 108 has a periodic structure and disperses the entered interference light. The interference light dispersed by the diffraction grating 108 is formed as an image on the line sensor 111 by the imaging lens 109 which can change a focusing state. The line sensor 111 detects the image-formed interference light as an image signal and outputs as the image signal regarding the subject's eye E (specifically, the fundus Er of the subject's eye E according to the present exemplary embodiment) to the image processing unit 150.

The operation unit 140 includes the imaging switch 144. When an examiner or the like operates the imaging switch 144, image capturing for obtaining an image regarding the subject's eye E (specifically, a tomographic image according to the present exemplary embodiment) is started from the moment.

The operation unit 140 includes the luminance increasing operation unit 145 and the luminance decreasing operation unit 146 and is configured to change luminance of the above-described image in response to an operation performed by an examiner or the like on these operation units. In the present specification, luminance of an image is applied, for example, as intensity of the image according to an aspect of the present invention. Thus, for example, the luminance increasing operation unit 145 and the luminance decreasing operation unit 146 respectively constitute examples of an intensity increasing operation unit and an intensity decreasing operation unit according to the present invention.

The operation unit 140 includes the imaging mode switching operation unit 147 and is configured to switch an imaging mode when an examiner or the like operates the imaging mode switching operation unit 147.

Figure 2:
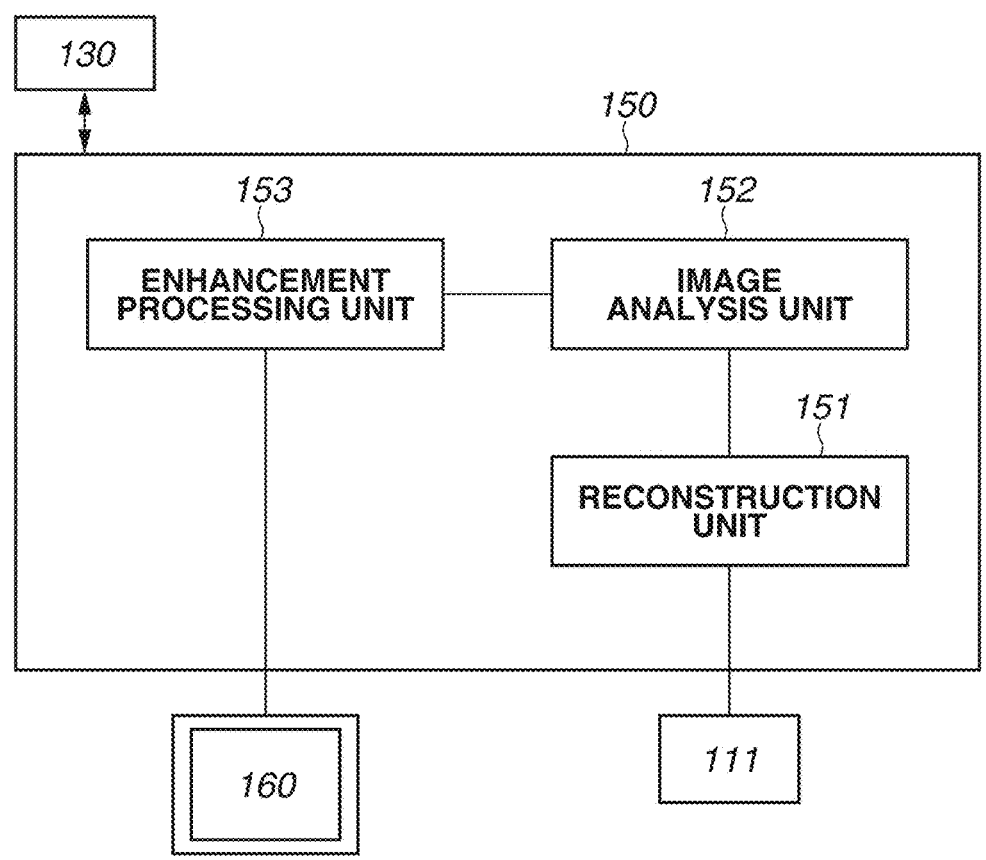
FIG. 2 illustrates an example of an internal configuration of an image processing unit illustrated in FIG. 1.

FIG. 2 illustrates an example of an internal configuration of the image processing unit 150 illustrated in FIG. 1. FIG. 2 also illustrates the control unit 130, the display unit 160, and the line sensor 111 illustrated in FIG. 1.

The image processing unit 150 is constituted of a reconstruction unit 151, an image analysis unit 152, and an enhancement processing unit 153 as illustrated in FIG. 2.

The reconstruction unit 151 generates original data of a tomographic image regarding the subject's eye E (specifically, the fundus Er of the subject's eye E according to the present exemplary embodiment) based on the image signal output from the line sensor 111. The ophthalmologic imaging apparatus 100 according to the present exemplary embodiment is, for example, a Fourier domain type apparatus, and the reconstruction unit 151 generates the original data of the tomographic image of the subject's eye E by performing wavenumber conversion, Fourier transform, and logarithmic transformation on the output signal from the line sensor 111. The ophthalmologic imaging apparatus 100 is described here as the Fourier domain type apparatus, however, is not limited thereto, and may be, for example, a time domain type apparatus or a wavelength sweeping type apparatus utilizing a light source of which wavelength is changed with the passage of time even the same Fourier domain type apparatus The image analysis unit 152 performs processing for analyzing the original data of the tomographic image generated by the reconstruction unit 151. More specifically, the image analysis unit 152 analyzes the original data of the tomographic image of the subject's eye E and detects a structure of the subject's eye E included in the original data of the tomographic image.

The enhancement processing unit 153 performs luminance change processing on the original data of the tomographic image of the subject's eye E. Further, the enhancement processing unit 153 can output the tomographic image subjected to the enhancement processing to the display unit 160 and display the tomographic image on the display unit 160.

At least a part of each configuration in the image processing unit 150 may be implemented as an independent device. The image processing unit 150 may be configured as an electrical circuit by an image processing board. Further, each configuration in the image processing unit 150 may be a software configuration which implements function thereof by a central processing unit (CPU) of a computer executing a program. According to the present exemplary embodiment, each configuration in the image processing unit 150 is a software configuration. In this case, the CPU of the computer executes a program stored in a random access memory (RAM) and a read-only memory (ROM) to entirely control the computer and execute a function of each configuration. In this regard, the RAM includes an area for temporarily storing a program loaded from, for example, a storage medium drive and a work area for the CPU to perform various types of processing. Further, the ROM stores various programs of the computer and the like.

Next, a control method is described for capturing the tomographic image of the subject's eye E by the ophthalmologic imaging apparatus 100 according to the first exemplary embodiment of the present invention.

First, an examiner sits an examinee, i.e., a patient in front of the ophthalmologic imaging apparatus 100 and starts OCT imaging. In the OCT imaging, the light output from the light source 101 in FIG. 1 passes through the optical fiber 102*a* and is branched by the light branch unit 103 into the measurement light directed toward the subject's eye E and the reference light directed toward the reflection mirror 106.

The measurement light directed toward the subject's eye E passes through the optical fiber 102*b* and is output from the fiber end thereof. Further, the measurement light is approximately parallelized by the optical system 121 and enters the scanning unit 122. The measurement light deflected by the galvano mirrors of the scanning unit 122 illuminates the subject's eye E (specifically, the fundus Er of the subject's eye E according to the present exemplary embodiment) via the lens 123. The reflected light reflected by the subject's eye E passes through the path in reverse and returns to the light branch unit 103.

On the other hand, the reference light directed toward the reflection mirror 106 passes through the optical fiber 102*c*, is output from the fiber end thereof, and then reaches the reflection mirror 106 via the collimate optical system 104 and the dispersion compensation optical system 105. The reference light reflected by the reflection mirror 106 passes through the path in reverse and returns to the light branch unit 103.

The measurement light and the reference light returned to the light branch unit 103 interferes with each other and become the interference light, and the interference light passes through the optical fiber 102*d*, is approximately parallelized by the lens 107, and enters the diffraction grating 108. The interference light input into the diffraction grating 108 is formed as an image on the line sensor 111 by the imaging lens 109 and detected by the line sensor 111 as the image signal at one point on the subject's eye E (specifically, the fundus Er of the subject's eye E according to the present exemplary embodiment).

The image signal obtained by the line sensor 111 is output to the image processing unit 150. According to the present exemplary embodiment, the image signal output from the line sensor 111 is 12-bit integer type data. The reconstruction unit 151 in the image processing unit 150 performs wavenumber conversion, Fast Fourier transform (FFT), and logarithmic transformation processing on the 12-bit integer type data and generates original data of the tomographic image in a depth direction at one point on the subject's eye E (specifically, the fundus Er of the subject's eye E according to the present exemplary embodiment). According to the present exemplary embodiment, the original data of the tomographic image generated by the reconstruction unit 151 is 32-bit floating point type data.

After the image signal at one point on the subject's eye E is obtained, the scanning unit 122 drives the galvano mirrors based on control of the control unit 130 and generates the interference light at another point on the subject's eye E. The interference light at the another point is generated as the original data of the tomographic image in the depth direction at the another point on the subject's eye E via the line sensor 111 and the reconstruction unit 151. A series of the above-described processing is repeated, and thus the original data of one piece of the tomographic image of the subject's eye E (specifically, the fundus Er of the subject's eye E according to the present exemplary embodiment) can be generated.

According to the first exemplary embodiment, the ophthalmologic imaging apparatus 100 can generate the tomographic image of the subject's eye E (specifically, the fundus Er of the subject's eye E according to the present exemplary embodiment) by three generation methods. These three tomographic image generation methods are described below.

A first tomographic image generation method is a normal generation method for generating a tomographic image by performing laser scanning only once on a region including the subject's eye E.

A second tomographic image generation method is a method for changing luminance of a tomographic image obtained by performing laser scanning on a region including the subject's eye E. The second tomographic image generation method is described with reference to FIGS. 3A to 3D.

FIGS. 3A to 3D illustrate the second tomographic image generation method of the ophthalmologic imaging apparatus 100 according to the first exemplary embodiment of the present invention.

Figure 3A:
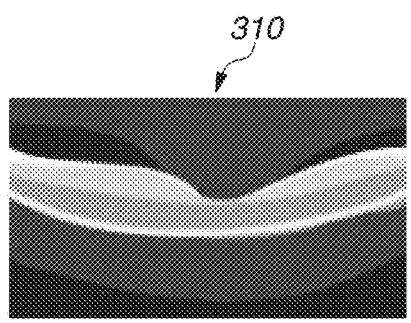
FIGS. 3A to 3D illustrate a second tomographic image generation method of the ophthalmologic imaging apparatus according to the first exemplary embodiment of the present invention.
Figure 3B:
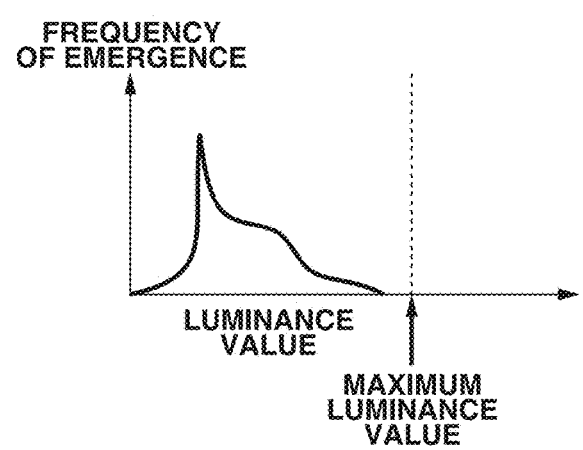

FIG. 3A illustrates an example of a tomographic image 310 of the fundus Er of the subject's eye E, and FIG. 3B illustrates a histogram representing a relationship between a luminance value and a frequency of emergence of the tomographic image 310 illustrated in FIG. 3A. In the tomographic image 310 illustrated in FIG. 3A, image luminance of a retinal region is high, and a structure thereof can be observed, however, image luminance of a vitreous body region and a choroid coat region is low, and it is difficult to observe structures thereof. From the histogram illustrated in FIG. 3B, it can be seen that many pixels of which the luminance values are low appear.

Figure 3C:
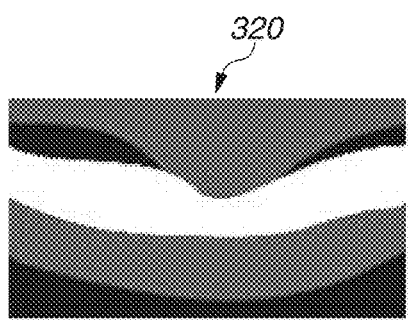
Figure 3D:
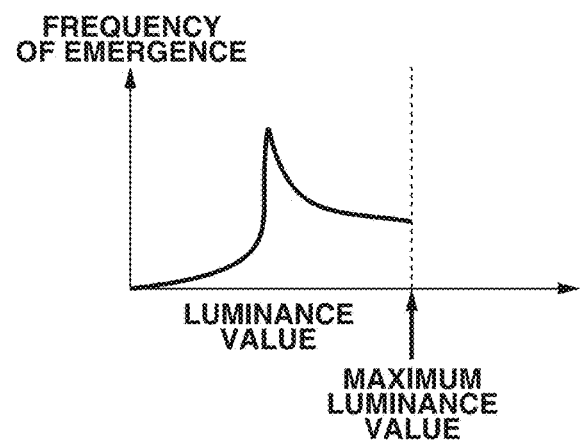

Thus, FIG. 3C illustrates a tomographic image 320 which is obtained by doubling the luminance value of the tomographic image 310 illustrated in FIG. 3A, and FIG. 3D illustrates a histogram representing a relationship between a luminance value and a frequency of emergence of the tomographic image 320 illustrated in FIG. 3C. From FIGS. 3C and 3D, it can be seen that the retinal region causes saturation, and it is difficult to observe the structure thereof, however, the image luminance of the vitreous body region and the choroid coat region becomes higher, and the structures thereof can be observed. The processing for changing the luminance of the tomographic image is performed by the enhancement processing unit 153. As described above, the enhancement processing unit 153 multiplies the luminance of the tomographic image by m, and thus a region of the subject's eye E having the low luminance can be observed. The second tomographic image generation method can obtain the tomographic image having high luminance at high speed.

A third tomographic image generation method is a generation method for generating one piece of a tomographic image by averaging luminance of a plurality of tomographic images obtained by performing laser scanning a plurality of times on the same region of the subject's eye E. The third tomographic image generation method is described with reference to FIG. 4.

Figure 4:
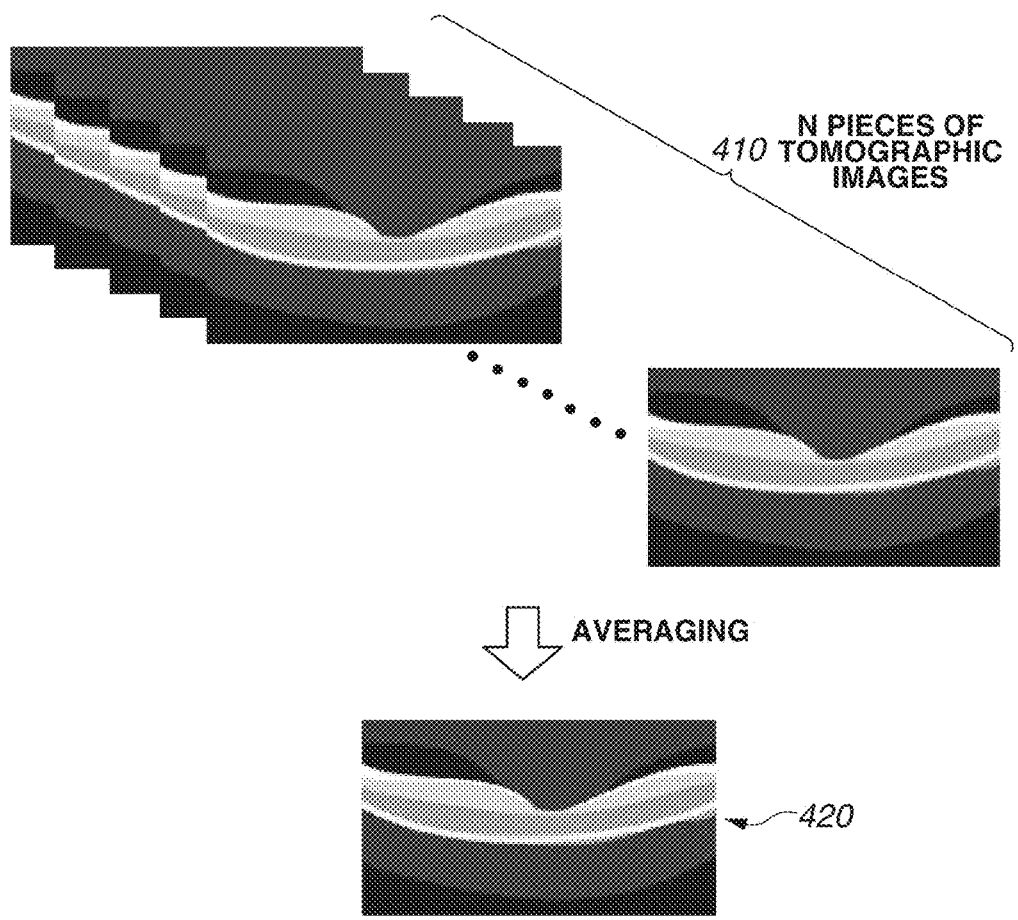
FIG. 4 illustrates a third tomographic image generation method of the ophthalmologic imaging apparatus according to the first exemplary embodiment of the present invention.

FIG. 4 illustrates the third tomographic image generation method of the ophthalmologic imaging apparatus 100 according to the first exemplary embodiment of the present invention.

As illustrated in FIG. 4, in the third tomographic image generation method, first, the same region of the subject's eye E is subjected to the laser scanning N times (here, N is an integer greater than or equal to two), and N pieces of tomographic images 410 are obtained. Next, the reconstruction unit 151 averages the luminance of the N pieces of the tomographic images 410 and generates one piece of a tomographic image 420. According to the third tomographic image generation method, the tomographic image less affected by noise can be obtained.

According to the present exemplary embodiment, for example, the first tomographic image generation method is used when the retinal region is previewed, the second tomographic image generation method is used when the vitreous body region or the choroid coat region is previewed, and the third tomographic image generation method is used when a final image is to be obtained, so that a preferable image can be obtained.

Figure 5:
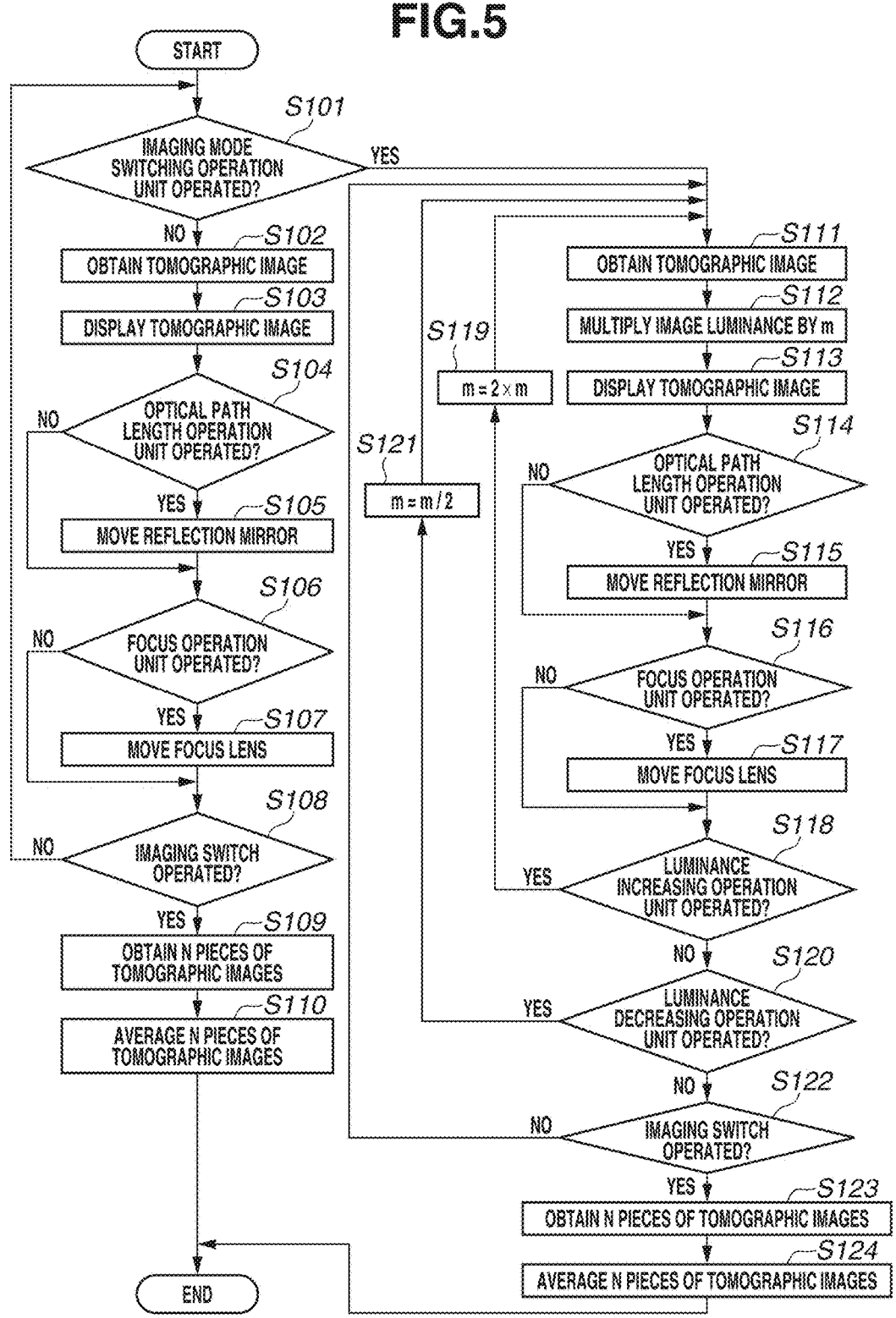
FIG. 5 is a flowchart illustrating an example of processing procedures in a control method of the ophthalmologic imaging apparatus according to the first exemplary embodiment of the present invention.

Next, processing procedures in a control method of the ophthalmologic imaging apparatus 100 according to the present exemplary embodiment are described. FIG. 5 is a flowchart illustrating an example of the processing procedures in the control method of the ophthalmologic imaging apparatus 100 according to the first exemplary embodiment of the present invention. In the descriptions of the flowchart in FIG. 5, it is assumed that the imaging mode switching operation unit 147 has a first imaging mode for suitably capturing an image of the retinal region (a first region) of the subject's eye E and a second imaging mode for suitably capturing an image of the vitreous body region (a second region) of the subject's eye E as switchable imaging modes. The second imaging mode is an imaging mode for obtaining the tomographic image of the vitreous body region more suitable than other region. Further, it is assumed that the first imaging mode is set at a start point of the flowchart in FIG. 5.

First, in step S101, the control unit 130 determines whether the imaging mode switching operation unit 147 is operated.

As a result of the determination in step S101, when the imaging mode switching operation unit 147 is not operated (NO in step S101), the control unit 130 selects the first imaging mode (the imaging mode for suitably capturing an image of the retinal region of the subject's eye E) which is currently set. The control unit 130 which performs the processing for selecting one imaging mode (for selecting the first imaging mode in the present step) from the first imaging mode and the second imaging mode constitutes a selection unit. Subsequently, the control unit 130 advances the processing to step S102 to execute processing in the first imaging mode.

In step S102, the image processing unit 150 (specifically, the reconstruction unit 151) successively obtains the tomographic images (specifically, the original data pieces of the tomographic images) of the subject's eye E based on the image signals successively output from the line sensor 111 according to the control of the control unit 130. The image processing unit 150 (specifically, the reconstruction unit 151) which performs the processing for successively obtaining the tomographic images of the subject's eye E constitutes an obtainment unit. The tomographic image obtained in the present step in the first imaging mode constitutes a first tomographic image.

Subsequently, in step S103, the control unit 130 performs control to display the tomographic images successively obtained in step S102 on the display unit 160. The control unit 130 which performs the control to display the tomographic images on the display unit 160 constitutes a display control unit. According to the present exemplary embodiment, the control unit 130 performs control to display a moving image of the tomographic images successively obtained in step S102 on the display unit 160.

Subsequently, in step S104, the control unit 130 determines whether the optical path length operation unit 141 is operated.

As a result of the determination in step S104, when the optical path length operation unit 141 is operated (YES in step S104), the processing proceeds to step S105.

In step S105, the optical path length control unit 131 in the control unit 130 controls the reflection mirror 106 to move by an amount corresponding to an operation amount of the optical path length operation unit 141.

When the processing in step S105 is finished, or when it is determined in step S104 that the optical path length operation unit 141 is not operated (NO in step S104), the processing proceeds to step S106.

In step S106, the control unit 130 determines whether the focus operation unit 143 is operated.

As a result of the determination in step S106, when the focus operation unit 143 is operated (YES in step S106), the processing proceeds to step S107.

In step S107, the focus lens control unit 133 in the control unit 130 controls the focus lens 121b to move by an amount corresponding to an operation amount of the focus operation unit 143.

When the processing in step S107 is finished, or when it is determined in step S106 that the focus operation unit 143 is not operated (NO in step S106), the processing proceeds to step S108.

In step S108, the control unit 130 determines whether the imaging switch 144 is operated.

As a result of the determination in step S108, when the imaging switch 144 is not operated (NO in step S108), the processing returns to step S101, and the processing in step S101 and subsequent steps is performed again.

On the other hand, as a result of the determination in step S108, when the imaging switch 144 is operated (YES in step S108), the processing proceeds to step S109.

In step S109, the image processing unit 150 (specifically, the reconstruction unit 151) obtains N pieces of the tomographic images (specifically, the original data pieces of the tomographic images) of the subject's eye E based on the image signals output from the line sensor 111 according to the control of the control unit 130.

Subsequently, in step S110, the image processing unit 150 (specifically, the reconstruction unit 151) averages the luminance of the N pieces of the tomographic images obtained in step S109 and generates one piece of the tomographic image. When the processing in step S110 is finished, the imaging is terminated, and the processing in the flowchart in FIG. 5 is terminated. In step S110, it is not required to average all of the N pieces of the tomographic images, and for example, a plurality of the tomographic images excluding the tomographic images of which image qualities are lower than a threshold value from the N pieces of the tomographic images may be averaged. Further, a plurality of the tomographic images excluding the tomographic images of which movement amounts of the eye are larger than a threshold value from the N pieces of the tomographic images may be averaged, or a plurality of the tomographic images excluding the tomographic images in which blinking occurred from the N pieces of the tomographic images may be averaged.

As a result of the determination in step S101, when the imaging mode switching operation unit 147 is operated (YES in step S101), the control unit 130 determines that the operation is performed for switching the first imaging mode to the second imaging mode and selects the second imaging mode (the imaging mode for suitably capturing an image of the vitreous body region of the subject's eye E). Subsequently, the control unit 130 advances the processing to step S111 to execute processing in the second imaging mode.

In step S111, the image processing unit 150 (specifically, the reconstruction unit 151) successively obtains the tomographic images (specifically, the original data pieces of the tomographic images) of the subject's eye E based on the image signals successively output from the line sensor 111 according to the control of the control unit 130. The tomographic image obtained in the present step in the second imaging mode constitutes a second tomographic image.

Subsequently, in step S112, the image processing unit 150 (specifically, the enhancement processing unit 153) performs processing for multiplying luminance magnifications of the tomographic images successively obtained in step S111 by m according to the control of the control unit 130.

Subsequently, in step S113, the control unit 130 performs control to display the tomographic images obtained by the processing in step S102 on the display unit 160. The control unit 130 which performs the control to display the tomographic images on the display unit 160 constitutes the display control unit. According to the present exemplary embodiment, considering that the second imaging mode is the mode for suitably capturing an image of the vitreous body region (the second region) of the subject's eye E, and the vitreous body region is drawn in high luminance, it is desirable that the tomographic image (the second tomographic image) displayed in the present step is higher in the luminance than the tomographic image (the first tomographic image) displayed in step S103. According to the present exemplary embodiment, the control unit 130 performs control to display a moving image of the tomographic images successively obtained by the processing in step S112 on the display unit 160.

Subsequently, in step S114, the control unit 130 determines whether the optical path length operation unit 141 is operated.

As a result of the determination in step S114, when the optical path length operation unit 141 is operated (YES in step S114), the processing proceeds to step S115.

In step S115, the optical path length control unit 131 in the control unit 130 controls the reflection mirror 106 to move by an amount corresponding to the operation amount of the optical path length operation unit 141.

When the processing in step S115 is finished, or when it is determined in step S114 that the optical path length operation unit 141 is not operated (NO in step S114), the processing proceeds to step S116.

In step S116, the control unit 130 determines whether the focus operation unit 143 is operated.

As a result of the determination in step S116, when the focus operation unit 143 is operated (YES in step S116), the processing proceeds to step S117.

In step S117, the focus lens control unit 133 in the control unit 130 controls the focus lens 121b to move by an amount corresponding to the operation amount of the focus operation unit 143.

When the processing in step S117 is finished, or when it is determined in step S116 that the focus operation unit 143 is not operated (NO in step S116), the processing proceeds to step S118.

In step S118, the control unit 130 determines whether the luminance increasing operation unit 145 is operated.

As a result of the determination in step S118, when the luminance increasing operation unit 145 is operated (YES in step S118), the processing proceeds to step S119.

In step S119, the image processing unit 150 (specifically, the enhancement processing unit 153) performs processing for setting to double the luminance magnification m in step S112 according to the control of the control unit 130. Subsequently, the processing returns to step S111, and the processing in step S111 and subsequent steps is performed again.

On the other hand, as a result of the determination in step S118, when the luminance increasing operation unit 145 is not operated (NO in step S118), the processing proceeds to step S120.

In step S120, the control unit 130 determines whether the luminance decreasing operation unit 146 is operated.

As a result of the determination in step S120, when the luminance decreasing operation unit 146 is operated (YES in step S120), the processing proceeds to step S121.

In step S121, the image processing unit 150 (specifically, the enhancement processing unit 153) performs processing for setting to halve (½) the luminance magnification m in step S112 according to the control of the control unit 130. Subsequently, the processing returns to step S111, and the processing in step S111 and subsequent steps is performed again.

According to the present exemplary embodiment, the image processing unit 150 (specifically, the enhancement processing unit 153) which performs the processing for changing the luminance of the tomographic image in steps S112, S119, and S121 (specifically, processing for increasing the luminance according to the present exemplary embodiment) constitutes a luminance change unit (an intensity change unit according to an aspect of the present invention).

On the other hand, as a result of the determination in step S120, when the luminance decreasing operation unit 146 is not operated (NO in step S120), the processing proceeds to step S122.

In step S122, the control unit 130 determines whether the imaging switch 144 is operated.

As a result of the determination in step S122, when the imaging switch 144 is not operated (NO in step S122), the processing returns to step S111, and the processing in step S111 and subsequent steps is performed again.

On the other hand, as a result of the determination in step S122, when the imaging switch 144 is operated (YES in step S122), the processing proceeds to step S123.

In step S123, the image processing unit 150 (specifically, the reconstruction unit 151) obtains N pieces of the tomographic images (specifically, the original data pieces of the tomographic images) of the subject's eye E based on the image signals output from the line sensor 111 according to the control of the control unit 130.

Subsequently, in step S124, the image processing unit 150 (specifically, the reconstruction unit 151) averages the luminance of the N pieces of the tomographic images obtained in step S123 and generates one piece of the tomographic image. When the processing in step S124 is finished, the imaging is terminated, and the processing in the flowchart in FIG. 5 is terminated. In step S124, it is not required to average all of the N pieces of the tomographic images, and for example, a plurality of the tomographic images excluding the tomographic images of which image qualities are lower than a threshold value from the N pieces of the tomographic images may be averaged. In this regard, it is desirable to evaluate an image quality of the vitreous body region detected from the tomographic image. Further, a plurality of the tomographic images excluding the tomographic images of which movement amounts of the eye are larger than a threshold value from the N pieces of the tomographic images may be averaged, or a plurality of the tomographic images excluding the tomographic images in which blinking occurred from the N pieces of the tomographic images may be averaged. Furthermore, in step S124, it is desirable to obtain more pieces of the tomographic images than the number of the tomographic images obtained in step S110.

The ophthalmologic imaging apparatus 100 according to the first exemplary embodiment performs control to display the first tomographic image captured in the first imaging mode on the display unit 160 (step S103 in FIG. 5) when the first imaging mode for suitably capturing the image of the retinal region (the first region) of the subject's eye E is selected (NO in step S101 in FIG. 5) and performs control to display the second tomographic image which is captured in the second imaging mode and higher in the luminance than the first tomographic image on the display unit 160 (step S113 in FIG. 5) when the second imaging mode for suitably capturing the image of the vitreous body region (the second region) of the subject's eye E is selected (YES in step S101 in FIG. 5).

According to the above-described configuration, even a region is usually darkly drawn (in the low luminance) such as the vitreous body region, the tomographic image can be obtained in which the relevant region is clearly drawn. This configuration responds to needs of more detailed observation of inner structures of vitreous bodies in recent years. Accordingly, the ophthalmologic imaging apparatus 100 according to the first exemplary embodiment can appropriately observe structures in a plurality of regions in the subject's eye E. For example, when focus adjustment, optical path length adjustment (further, alignment adjustment), and the like are performed, the tomographic image in which each region is clearly drawn is displayed, so that a final tomographic image can be obtained after performing suitable adjustment.

In the above first exemplary embodiment, the example is described in which the luminance of the tomographic image is manually changed using the luminance increasing operation unit 145 and the luminance decreasing operation unit 146, however, the present invention is not limited to this embodiment. For example, the present invention can be applied to an embodiment in which the ophthalmologic imaging apparatus 100 automatically performs a luminance change in a tomographic image according to the luminance of the tomographic image. This embodiment is described below as a modification of the first exemplary embodiment with reference to FIGS. 6 and 7.

Figure 6:
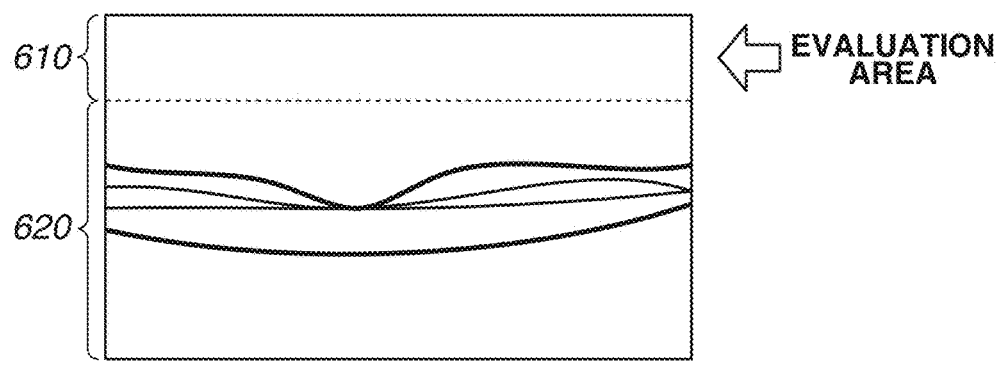
FIG. 6 illustrates a method for automatically changing luminance of a tomographic image according to a modification of the first exemplary embodiment of the present invention.
Figure 7:
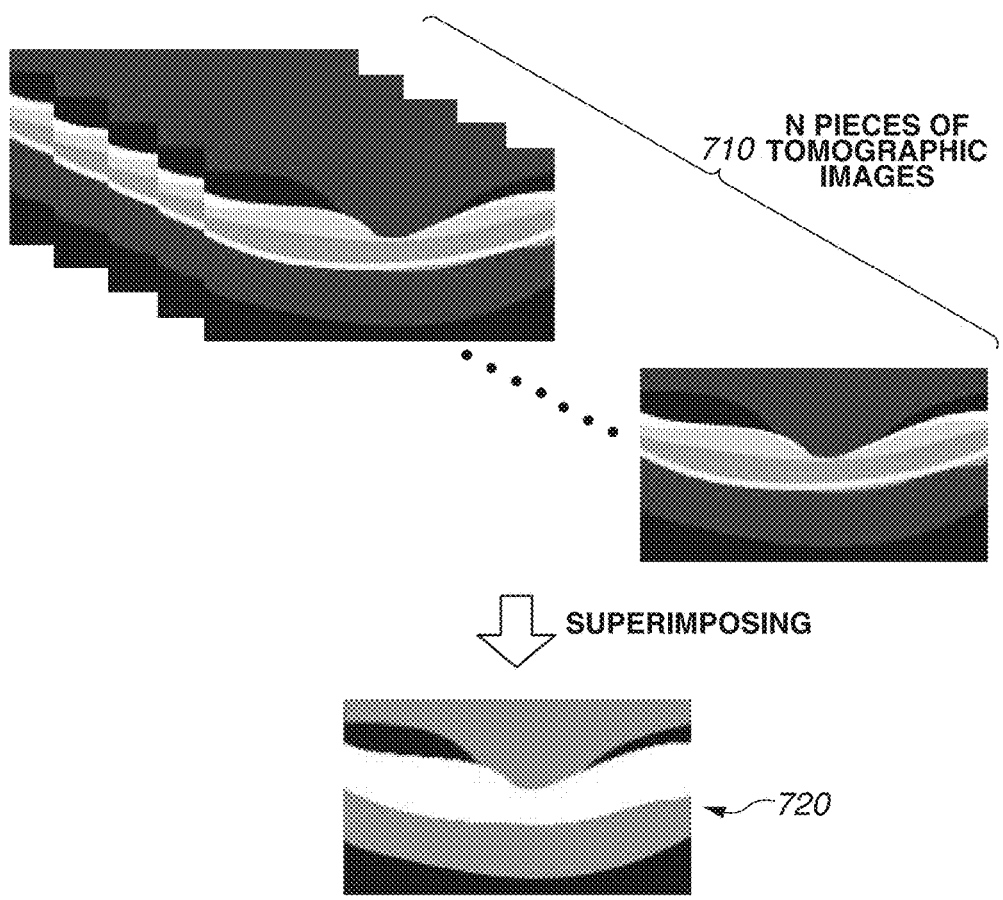
FIG. 7 illustrates a method for automatically changing luminance of a tomographic image according to the modification of the first exemplary embodiment of the present invention.

FIGS. 6 and 7 illustrate the modification of the first exemplary embodiment of the present invention and a method for automatically changing luminance of a tomographic image.

The retinal region of the subject's eye E is a region highly reflecting the illumination light. Thus, when the tomographic image of the retinal region is to be captured, the reflection mirror 106 for adjusting the optical path length and the focus lens 121b for adjusting the focus are automatically moved to increase the luminance of the light incident on the line sensor 111, and thus an observation image can be obtained almost in a suitable state. In the tomographic image at that time, the vitreous body region is displayed on an upper portion as illustrated in FIG. 7. In this case, for example, an area 610 in an upper quarter of a tomographic image illustrated in FIG. 6 is an area in which the vitreous body of the subject's eye E is mainly displayed. Thus, for example, the area 610 in the upper quarter is regarded as an evaluation area, and when the image luminance in the relevant area is lower or equal to a predetermined value, the luminance magnification m is automatically increased, so that vitreous body observation can be suitably performed. Specification of the evaluation area for automatically changing the luminance is not limited to the above-described method, and, for example, a method for selecting a vitreous body region by extracting a retinal region and the vitreous body region using a known recognition technique of a retinal tomographic image and a method for selecting an arbitrary region from the display unit 160 by an examiner may be used. An area 620 in a lower three-quarters is an area of the tomographic image illustrated in FIG. 6 is an area in which the retina of the subject's eye E is mainly displayed.

Further, the vitreous body region exists more inside of the subject's eye E than the retinal region, so that the reflection mirror 106 is moved from a position at which the luminance of the reflected light is the maximum to a direction shortening the optical path length by a predetermined amount, and the focus lens 121b is moved by a predetermined amount, and thus an excellent vitreous body image can be obtained with fewer operations.

Furthermore, according to the present exemplary embodiment, the optical path length control unit 131 in the control unit 130 performs control to place the reflection mirror 106 which is the optical path length adjustment optical unit for adjusting the optical path length of the reference light on a position at which the optical path length of the reference light (to move the reflection mirror 106 in a left direction in FIG. 1) is shorter when the second imaging mode is selected than when the first imaging mode is selected.

In the tomographic image obtained in the first imaging mode, for example, the vitreous body of the subject's eye E is mainly displayed in the area 610 in the upper quarter as described with reference to FIG. 6. Thus, in the second imaging mode, the reflection mirror 106 is placed on the position shortening the optical path length of the reference light than the case of the first imaging mode, and a position at which the vitreous body of the subject's eye E is mainly displayed is shifted downward than the area 610 in the upper quarter illustrated in FIG. 6 to come around the center so that an examiner can more easily observe the vitreous body.

Further, according to the present exemplary embodiment, the focus lens control unit 133 in the control unit 130 performs control to move the focus lens 121b which is the focus adjustment optical unit for adjusting the focus of the measurement light so that a focus position of the measurement light is closer to the ophthalmologic imaging apparatus 100 when the second imaging mode is selected than when the first imaging mode is selected.

Accordingly, the control unit 130 can be configured to perform control, when the tomographic image captured according to the selected imaging mode is displayed on the display unit 160, to move the adjustment optical unit included in the ophthalmologic imaging apparatus 100 according to the selected imaging mode.

Next, a second exemplary embodiment of the present invention is described.

A schematic configuration of an ophthalmologic imaging apparatus according to the second exemplary embodiment is similar to the schematic configuration of the ophthalmologic imaging apparatus 100 according to the first exemplary embodiment illustrated in FIG. 1. Further, an internal configuration of an image processing unit according to the second exemplary embodiment is similar to the internal configuration of the image processing unit 150 illustrated in FIG. 2.

According to the second exemplary embodiment, the ophthalmologic imaging apparatus 100 can generate a tomographic image of a subject's eye E (specifically, a fundus Er of the subject's eye E according to the present exemplary embodiment) by three generation methods. These three tomographic image generation methods are described below.

A first tomographic image generation method is a normal generation method for generating a tomographic image by performing laser scanning only once on a region including the subject's eye E.

A second tomographic image generation method is a generation method for generating one piece of a tomographic image 420 by averaging luminance of a plurality (N pieces) of tomographic images 410 obtained by performing laser scanning a plurality of times on the same region of the subject's eye E as illustrated in FIG. 4. According to the second tomographic image generation method, the tomographic image less affected by noise can be obtained.

A third tomographic image generation method is a generation method for generating one piece of a tomographic image 720 by superimposing a plurality (N pieces) of tomographic images 710 with each other which are obtained by performing laser scanning a plurality of times on the same region of the subject's eye E as illustrated in FIG. 7. According to the third tomographic image generation method, the tomographic image 720 of which image luminance is increased so that a low luminance region in the tomographic images 710 can be easily observed can be obtained.

Figure 8:
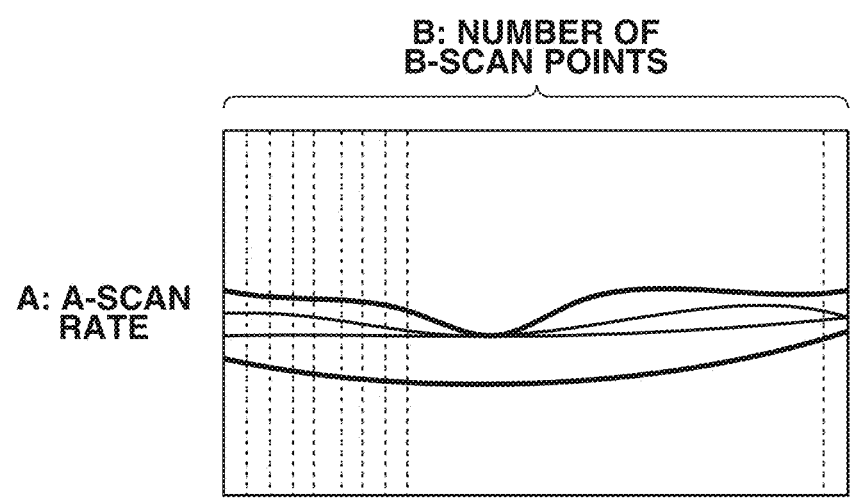
FIG. 8 illustrates a third tomographic image generation method of an ophthalmologic imaging apparatus according to a second exemplary embodiment of the present invention.

FIG. 8 illustrates the third tomographic image generation method of the ophthalmologic imaging apparatus 100 according to the second exemplary embodiment of the present invention.

A time t [sec] for obtaining one piece of the tomographic image can be expressed as a following formula (1) when an A-scan rate is A [Hz], and the number of B-scan points is B as illustrated in FIG. 8.

$$t=B/A \qquad (1)$$

Thus, for example, when the A-scan rate is 100 [kHz], and the number of B-scan points is 1024 points, a time used to obtain one piece of the tomographic image is about 10 [msec]. Thus, a time used to obtain three pieces of the tomographic images is about 30 [msec], and a frame rate for switching every three tomographic images is about [Hz]. An image having a frame rate of 33 [Hz] is equivalent to a common moving image, and a moving image without sense of incongruity can be obtained.

In addition, when a tomographic image having a higher luminance level is intended to be obtained, a total number of obtained tomographic images (Nm) is increased, and thus an intended result can be achieved. In this regard, the number of B-scan points may be decreased to maintain a real-time property. For example, when the number of B-scan points is halved, namely 512 points, a time used to obtain one piece of the tomographic image is about 5 [msec], and six pieces of the tomographic images can be obtained in the same 30 [msec]. Thus, double pieces of the tomographic images can be obtained.

The operation can be performed using, for example, the luminance increasing operation unit 145 and the luminance decreasing operation unit 146. For example, every time the luminance increasing operation unit 145 is operated, the total number of obtained tomographic images (Nm) is doubled, and the number of B-scan points is halved. In reverse, for example, every time the luminance decreasing operation unit 146 is operated, the total number of obtained tomographic images (Nm) is halved, and the number of B-scan points is doubled. Accordingly, a tomographic image having desired luminance can be obtained.

When the focus operation unit 143 and the optical path length operation unit 141 are operated, a state of the tomographic image is largely changed, so that superimposing is reset, and the image luminance is multiplied by Nm/n (Nm: the total number of obtained tomographic images, n: the number of obtained tomographic images) to maintain the equivalent image luminance.

A plurality of tomographic images is superimposed with each other as described in the third tomographic image generation method, and thus a tomographic image less affected by random noise and having high luminance can be obtained.

Figure 9B:
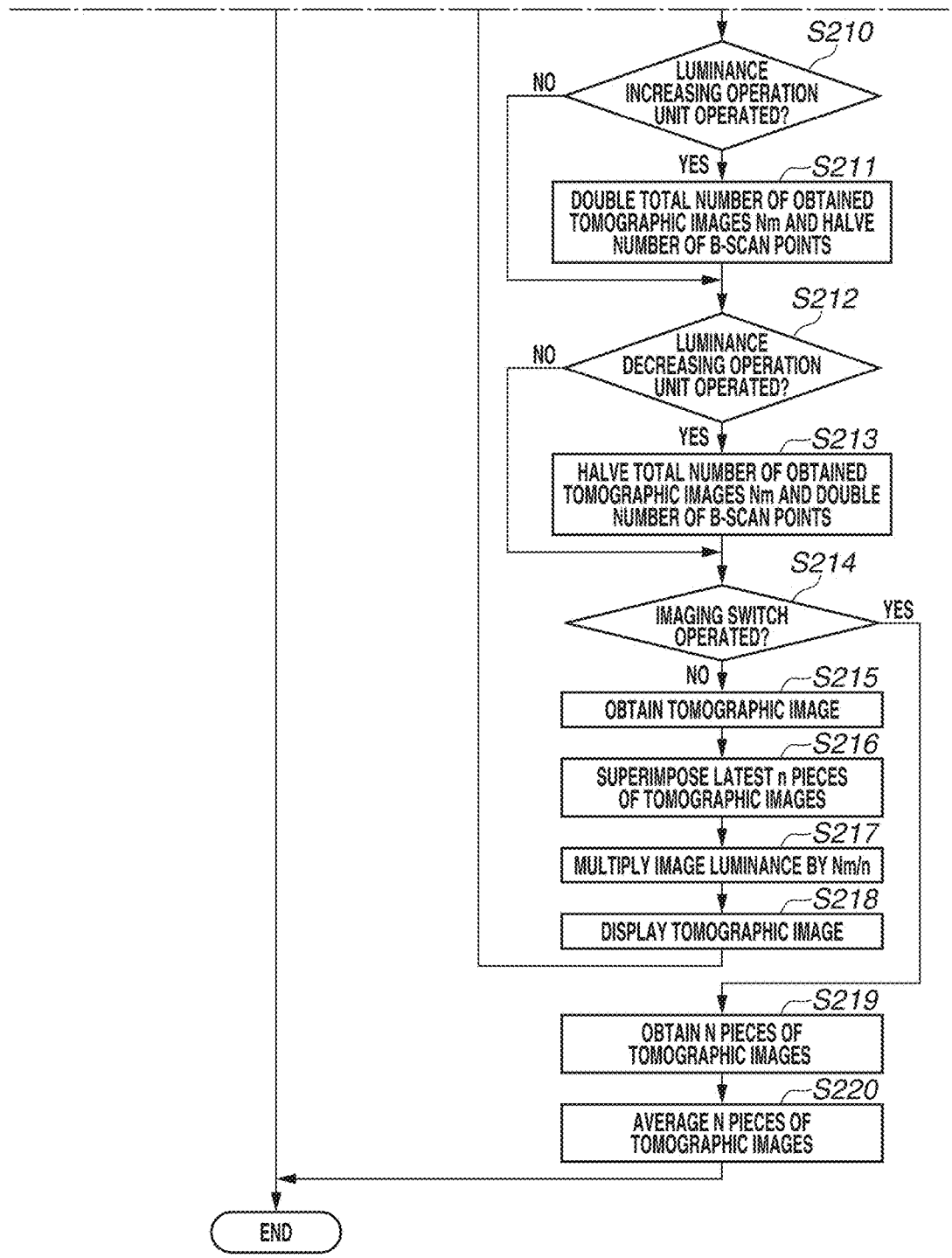
FIG. 9 (including FIGS. 9A and 9B) is a flowchart illustrating an example of processing procedures in a control method of the ophthalmologic imaging apparatus according to the second exemplary embodiment of the present invention.
Figure 10A:
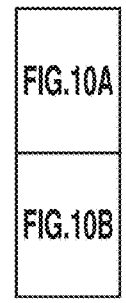
FIG. 10 (including FIGS. 10A and 10B) is a flowchart illustrating an example of processing procedures in a control method of an ophthalmologic imaging apparatus according to a third exemplary embodiment of the present invention.
Figure 10A:
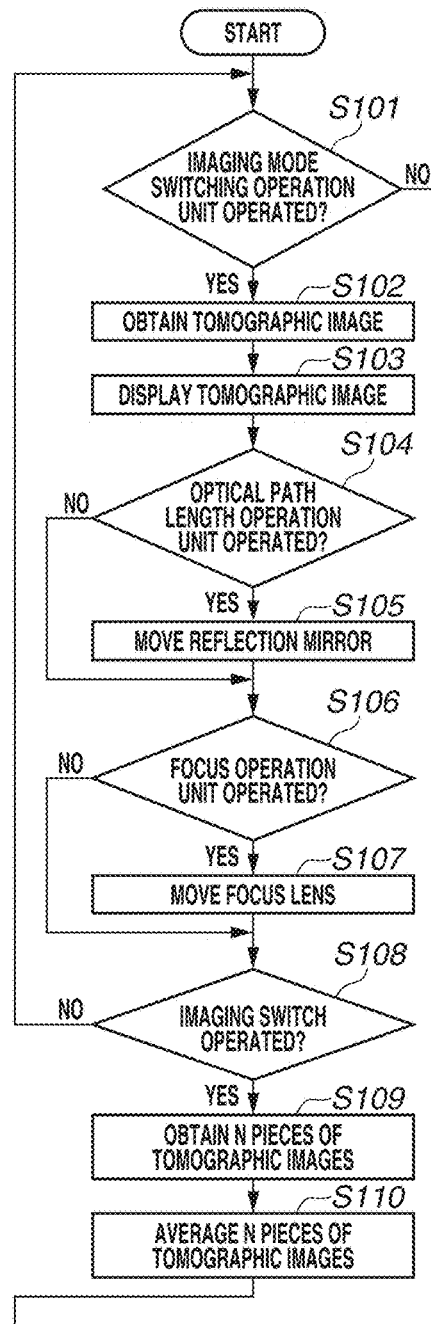
Figure 10A:
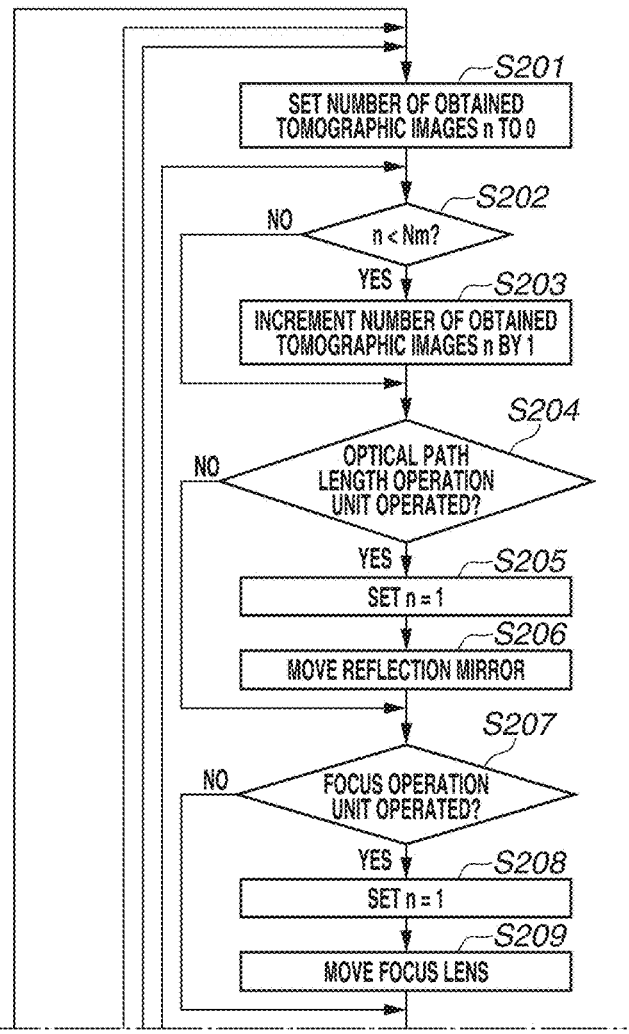
Figure 10B:
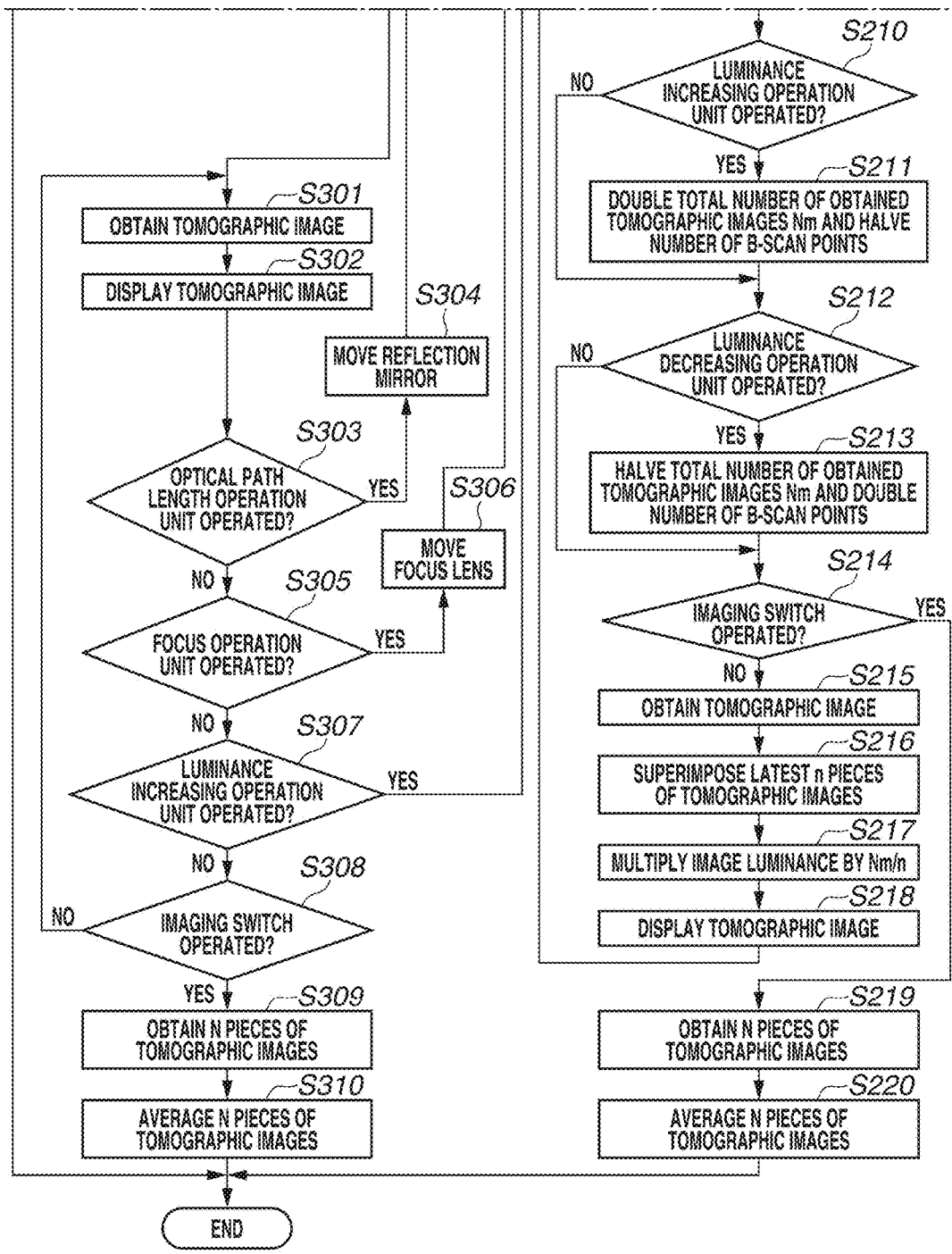

Next, processing procedures in a control method of the ophthalmologic imaging apparatus 100 according to the present exemplary embodiment are described. FIG. 9 (including FIGS. 9A and 9B) is a flowchart illustrating an example of the processing procedures in the control method of the ophthalmologic imaging apparatus 100 according to the second exemplary embodiment of the present invention. In FIG. 9, the processing steps similar to the processing steps illustrated in FIG. 5 are denoted by the same step numbers, and the detailed descriptions thereof are omitted. In the descriptions of the flowchart in FIG. 9, it is assumed that the imaging mode switching operation unit 147 has a first imaging mode for suitably capturing an image of the retinal region (a first region) of the subject's eye E and a second imaging mode for suitably capturing an image of the vitreous body region (a second region) of the subject's eye E as switchable imaging modes. Further, it is assumed that the first imaging mode is set at a start point of the flowchart in FIG. 9.

First, in step S101, the control unit 130 determines whether the imaging mode switching operation unit 147 is operated.

As a result of the determination in step S101, when the imaging mode switching operation unit 147 is not operated (NO in step S101), the control unit 130 selects the first imaging mode (the imaging mode for suitably capturing an image of the retinal region of the subject's eye E) which is currently set. The control unit 130 which performs the processing for selecting one imaging mode (for selecting the first imaging mode in the present step) from the first imaging mode and the second imaging mode constitutes the selection unit. Subsequently, the control unit 130 advances the processing to step S102 to execute processing in the first imaging mode and performs the processing in steps S102 to S110 as described in FIG. 5. When the processing in step S110 is finished, the processing in the flowchart in FIG. 9 is terminated.

On the other hand, as a result of the determination in step S101, when the imaging mode switching operation unit 147 is operated (YES in step S101), the control unit 130 determines that the operation is performed for switching the first imaging mode to the second imaging mode and selects the second imaging mode (the imaging mode for suitably capturing an image of the vitreous body region of the subject's eye E). Subsequently, the control unit 130 advances the processing to step S201 to execute processing in the second imaging mode.

In step S201, for example, the control unit 130 (or the image processing unit 150) performs processing for setting the number of obtained tomographic images n to zero.

Subsequently, in step S202, for example, the control unit 130 (or the image processing unit 150) determines whether the number of obtained tomographic images n is less than the total number of obtained tomographic images Nm.

As a result of the determination in step S202, when the number of obtained tomographic images n is less than the total number of obtained tomographic images Nm (YES in step S202), the processing proceeds to step S203.

In step S203, for example, the control unit 130 (or the image processing unit 150) performs processing for incrementing the number of obtained tomographic images n by one.

When the processing in step S203 is finished, or when it is determined in step S202 that the number of obtained tomographic images n is not less than the total number of obtained tomographic images Nm (NO in step S202), the processing proceeds to step S204.

In step S204, the control unit 130 determines whether the optical path length operation unit 141 is operated.

As a result of the determination in step S204, when the optical path length operation unit 141 is operated (YES in step S204), the processing proceeds to step S205.

In step S205, for example, the control unit 130 (or the image processing unit 150) performs processing for setting the number of obtained tomographic images n to one.

Subsequently, in step S206, the optical path length control unit 131 in the control unit 130 controls the reflection mirror 106 to move by an amount corresponding to an operation amount of the optical path length operation unit 141.

When the processing in step S206 is finished, or when it is determined in step S204 that the optical path length operation unit 141 is not operated (NO in step S204), the processing proceeds to step S207.

In step S207, the control unit 130 determines whether the focus operation unit 143 is operated.

As a result of the determination in step S207, when the focus operation unit 143 is operated (YES in step S207), the processing proceeds to step S208.

In step S208, for example, the control unit 130 (or the image processing unit 150) performs the processing for setting the number of obtained tomographic images n to one.

Subsequently, in step S209, the focus lens control unit 133 in the control unit 130 controls the focus lens 121b to move by an amount corresponding to an operation amount of the focus operation unit 143.

When the processing in step S209 is finished, or when it is determined in step S207 that the focus operation unit 143 is not operated (NO in step S207), the processing proceeds to step S210.

In step S210, the control unit 130 determines whether the luminance increasing operation unit 145 is operated.

As a result of the determination in step S210, when the luminance increasing operation unit 145 is operated (YES in step S210), the processing proceeds to step S211.

In step S211, for example, the control unit 130 performs a setting to double the total number of obtained tomographic images Nm and halve the number of B-scan points.

When the processing in step S211 is finished, or when it is determined in step S210 that the luminance increasing operation unit 145 is not operated (NO in step S210), the processing proceeds to step S212.

In step S212, the control unit 130 determines whether the luminance decreasing operation unit 146 is operated.

As a result of the determination in step S212, when the luminance decreasing operation unit 146 is operated (YES in step S212), the processing proceeds to step S213.

In step S213, for example, the control unit 130 performs a setting to halve the total number of obtained tomographic images Nm and double the number of B-scan points.

When the processing in step S213 is finished, or when it is determined in step S212 that the luminance decreasing operation unit 146 is not operated (NO in step S212), the processing proceeds to step S214.

In step S214, the control unit 130 determines whether the imaging switch 144 is operated.

As a result of the determination in step S214, when the imaging switch 144 is not operated (NO in step S214), the processing proceeds to step S215.

In step S215, the image processing unit 150 (specifically, the reconstruction unit 151) obtains one piece of the tomographic image (specifically, the original data of the tomographic image) of the subject's eye E based on the image signal output from the line sensor 111 according to the control of the control unit 130. The image processing unit 150 (specifically, the reconstruction unit 151) which performs the processing for obtaining the tomographic image of the subject's eye E constitutes the obtainment unit.

Subsequently, in step S216, the image processing unit 150 (specifically, the reconstruction unit 151) performs processing for superimposing the latest n pieces of the tomographic images with each other and generating one piece of the tomographic image as a composite image. According to the present exemplary embodiment, the image processing unit 150 (specifically, the reconstruction unit 151) successively generates the composite images every time the processing in step S216 is repeatedly performed (specifically, every time one piece of the tomographic image is obtained in step S215). The image processing unit 150 (specifically, the reconstruction unit 151) which performs the processing for successively generating the composite images constitutes a generation unit. In other words, the image processing unit 150 (specifically, the reconstruction unit 151) constituting the generation unit successively generates the composite images as the second tomographic images so that the intensity thereof become higher than that of the first tomographic image obtained in the first imaging mode. Further, the image processing unit 150 (specifically, the reconstruction unit 151) constituting the generation unit sets an area to be a reference of position adjustment before performing superimposition of the tomographic images of the subject's eye E closer to a coherence gate side when the second imaging mode is selected than when the first imaging mode is selected, adjusts positions of a plurality of the tomographic images based on the set area when the second imaging mode is selected, and successively generates the composite images by superimposing the plurality of the tomographic images subjected to the position adjustment with each other.

Subsequently, in step S217, the image processing unit 150 (specifically, the enhancement processing unit 153) performs processing for multiplying the luminance of the tomographic image (the composite image) generated in step S216 by Nm/n. The image processing unit 150 (specifically, the enhancement processing unit 153) which performs the processing in step S217 constitutes the luminance change unit (the intensity change unit according to an aspect of the present invention).

Subsequently, in step S218, the control unit 130 performs control to display the tomographic image (the composite image) obtained by the processing in step S217 on the display unit 160. The control unit 130 which performs the control to display the tomographic image (the composite image) on the display unit 160 constitutes the display control unit. According to the present exemplary embodiment, considering that the second imaging mode is the mode for suitably capturing an image of the vitreous body region (the second region) of the subject's eye E, and the vitreous body region is drawn in high luminance, it is desirable that the tomographic image (the second tomographic image) of the composite image displayed in the present step is higher in the luminance than the tomographic image (the first tomographic image) displayed in step S103. Further, according to the present exemplary embodiment, the control unit 130 performs control to display a moving image of the tomographic images (the composite images) successively generated in step S216 and then successively subjected to the processing for changing the luminance in step S217 on the display unit 160. Subsequently, the processing returns to step S202, and the processing in step S202 and subsequent steps is performed again.

As a result of the determination in step S214, when the imaging switch 144 is operated (YES in step S214), the processing proceeds to step S219.

In step S219, the image processing unit 150 (specifically, the reconstruction unit 151) obtains N pieces of the tomographic images (specifically, the original data pieces of the tomographic images) of the subject's eye E based on the image signals output from the line sensor 111 according to the control of the control unit 130.

Subsequently, in step S220, the image processing unit 150 (specifically, the reconstruction unit 151) averages the luminance of the N pieces of the tomographic images obtained in step S219 and generates one piece of the tomographic image. When the processing in step S220 is finished, the imaging is terminated, and the processing in the flowchart in FIG. 9 is terminated. In step S220, it is not required to average all of the N pieces of the tomographic images, and for example, a plurality of the tomographic images excluding the tomographic images of which image qualities are lower than a threshold value from the N pieces of the tomographic images may be averaged. In this regard, it is desirable to evaluate an image quality of the vitreous body region detected from the tomographic image. Further, a plurality of the tomographic images excluding the tomographic images of which movement amounts of the eye are larger than a threshold value from the N pieces of the tomographic images may be averaged, or a plurality of the tomographic images excluding the tomographic images in which blinking occurred from the N pieces of the tomographic images may be averaged. Furthermore, in step S220, it is desirable to obtain more pieces of the tomographic images than the number of the tomographic images obtained in step S110.

According to the processing in the flowchart in FIG. 9, in step S216, the processing for generating one piece of the tomographic image as the composite image is performed by superimposing the latest n pieces of the tomographic images with each other, however, the present exemplary embodiment is not limited to this aspect. For example, the present exemplary embodiment can be applied to an aspect that the image processing unit 150 (specifically, the reconstruction unit 151) changes the number of tomographic images to be superimposed to generate the composite image. The image processing unit 150 (specifically, the reconstruction unit 151) which performs the processing for changing the number of tomographic images to be superimposed constitutes a number-of-pieces change unit. In this case, following aspects can be considered.

As a first aspect for changing the number of tomographic images to be superimposed, an aspect can be considered in which the image processing unit 150 (specifically, the reconstruction unit 151) changes the number of tomographic images to be superimposed according to the luminance of the composite image generated in the latest. In the first aspect, for example, the image processing unit 150 (specifically, the reconstruction unit 151) first determines the composite image as a high luminance image when the luminance of the entire composite image is greater than or equal to a first threshold value, determines the composite image as a medium luminance image when the luminance of the entire composite image is less than the first threshold value and greater than or equal to a second threshold value which is less than the first threshold value, and determines the composite image as a low luminance image when the luminance of the entire composite image is less than the second threshold value. Subsequently, when the composite image generated in the latest is the high luminance image, the image processing unit 150 (specifically, the reconstruction unit 151) determines that the composite image of which luminance is more than enough is generated at the present moment and changes, for example, to decrease the number of tomographic images to be superimposed. Further, when the composite image generated in the latest is the medium luminance image, the image processing unit 150 (specifically, the reconstruction unit 151) determines that the composite image of which luminance is sufficient is generated at the present moment and performs processing, for example, to regard the number of tomographic images to be superimposed to the currently set number. Furthermore, when the composite image generated in the latest is the low luminance image, the image processing unit 150 (specifically, the reconstruction unit 151) determines that the composite image of which luminance is not sufficient is generated at the present moment and changes, for example, to increase the number of tomographic images to be superimposed.

As a second aspect for changing the number of tomographic images to be superimposed, an aspect can be considered in which the image processing unit 150 (specifically, the reconstruction unit 151) changes the number of tomographic images to be superimposed according to the luminance of the vitreous body region (the second region) in the composite image generated in the latest. In the second aspect, for example, the image processing unit 150 (specifically, the reconstruction unit 151) first determines whether the composite image is the high luminance image, the medium luminance image, or the low luminance image according to the luminance of the vitreous body region (for example, the area 610 illustrated in FIG. 6) in the composite image using the method similar to the one in the above-described first aspect. Subsequently, the image processing unit 150 (specifically, the reconstruction unit 151) performs processing for changing the number of tomographic images to be superimposed using the method similar to the one in the above-described first aspect.

The ophthalmologic imaging apparatus 100 according to the second exemplary embodiment changes the number of tomographic images to be superimposed when generating the composite image in addition to the processing according to the first exemplary embodiment and thus can obtain the tomographic image in which a region usually darkly drawn (in the low luminance) such as the vitreous body region is clearly drawn while improving efficiency of image processing. Accordingly, the ophthalmologic imaging apparatus 100 according to the second exemplary embodiment can appropriately observe structures in a plurality of regions in the subject's eye E. For example, a bright tomographic image less affected by random noise in which each region is clearly drawn can be displayed at the time of the focus adjustment, the optical path length adjustment, (further, the alignment adjustment), and the like, so that a final tomographic image can be obtained after performing suitable adjustment.

Further, according to the second exemplary embodiment, a method for automatically changing the total number of obtained tomographic images Nm from the luminance of the vitreous body region in the tomographic image may be used following the automatic change of the luminance of the tomographic image according to the above-described first exemplary embodiment.

Next, a third exemplary embodiment of the present invention is described.

According to the third exemplary embodiment, a timing to start superimposing of the tomographic images is not a timing when the imaging mode switching operation unit 147 is operated according to the second exemplary embodiment but a timing when detailed adjustment is performed. Generally, in imaging by an ophthalmologic imaging apparatus assuming an optical interference tomograph meter, a position of a main body is roughly adjusted with respect to a subject's eye E, and then the focus adjustment, the optical path length adjustment, and detailed position adjustment are performed. At a timing when the position is roughly adjusted, the tomographic image is largely changed, so that if the tomographic images are superimposed at that timing, an excellent tomographic image cannot be obtained. Thus, the third exemplary embodiment adopts an embodiment in which superimposing of the tomographic images is started when the detailed adjustment is started.

A schematic configuration of an ophthalmologic imaging apparatus according to the third exemplary embodiment is similar to the schematic configuration of the ophthalmologic imaging apparatus 100 according to the first exemplary embodiment illustrated in FIG. 1. Further, an internal configuration of an image processing unit according to the third exemplary embodiment is similar to the internal configuration of the image processing unit 150 illustrated in FIG. 2.

Next, processing procedures in a control method of the ophthalmologic imaging apparatus 100 according to the present exemplary embodiment are described. FIG. 10 (including FIGS. 10A and 10B) is a flowchart illustrating an example of the processing procedures in the control method of the ophthalmologic imaging apparatus 100 according to the third exemplary embodiment of the present invention. In FIG. 10, the processing steps similar to the processing steps illustrated in FIGS. 5 and 9 are denoted by the same step numbers, and the detailed descriptions thereof are omitted. In the descriptions of the flowchart in FIG. 10, it is assumed that the imaging mode switching operation unit 147 has a first imaging mode for suitably capturing an image of the retinal region (a first region) of the subject's eye E and a second imaging mode for suitably capturing an image of the vitreous body region (a second region) of the subject's eye E as switchable imaging modes. Further, it is assumed that the first imaging mode is set at a start point of the flowchart in FIG. 10.

First, in step S101, the control unit 130 determines whether the imaging mode switching operation unit 147 is operated.

As a result of the determination in step S101, when the imaging mode switching operation unit 147 is not operated (NO in step S101), the control unit 130 selects the first imaging mode (the imaging mode for suitably capturing an image of the retinal region of the subject's eye E) which is currently set. The control unit 130 which performs the processing for selecting one imaging mode (for selecting the first imaging mode in the present step) from the first imaging mode and the second imaging mode constitutes the selection unit. Subsequently, the control unit 130 advances the processing to step S102 to execute processing in the first imaging mode and performs the processing in steps S102 to S110 as described in FIG. 5. When the processing in step S110 is finished, the processing in the flowchart in FIG. 10 is terminated.

On the other hand, as a result of the determination in step S101, when the imaging mode switching operation unit 147 is operated (YES in step S101), the control unit 130 determines that the operation is performed for switching the first imaging mode to the second imaging mode and selects the second imaging mode (the imaging mode for suitably capturing an image of the vitreous body region of the subject's eye E). Subsequently, the control unit 130 advances the processing to step S301 to execute processing in the second imaging mode.

In step S301, the image processing unit 150 (specifically, the reconstruction unit 151) obtains the tomographic image (specifically, the original data of the tomographic image) of the subject's eye E based on the image signal output from the line sensor 111 according to the control of the control unit 130.

Subsequently, in step S302, the control unit 130 performs control to display the tomographic image obtained in step S301 on the display unit 160.

Subsequently, in step S303, the control unit 130 determines whether the optical path length operation unit 141 is operated.

As a result of the determination in step S303, when the optical path length operation unit 141 is operated (YES in step S303), the processing proceeds to step S304.

In step S304, the optical path length control unit 131 in the control unit 130 controls the reflection mirror 106 to move by an amount corresponding to an operation amount of the optical path length operation unit 141.

On the other hand, as a result of the determination in step S303, when the optical path length operation unit 141 is not operated (NO in step S303), the processing proceeds to step S305.

In step S305, the control unit 130 determines whether the focus operation unit 143 is operated.

As a result of the determination in step S305, when the focus operation unit 143 is operated (YES in step S305), the processing proceeds to step S306.

In step S306, the focus lens control unit 133 in the control unit 130 controls the focus lens 121b to move by an amount corresponding to an operation amount of the focus operation unit 143.

On the other hand, as a result of the determination in step S305, when the focus operation unit 143 is not operated (NO in step S305), the processing proceeds to step S307.

In step S307, the control unit 130 determines whether the luminance increasing operation unit 145 is operated.

As a result of the determination in step S307, when the luminance increasing operation unit 145 is not operated (NO in step S307), the processing proceeds to step S308.

In step S308, the control unit 130 determines whether the imaging switch 144 is operated.

As a result of the determination in step S308, when the imaging switch 144 is not operated (NO in step S308), the processing returns to step S301, and the processing in step S301 and subsequent steps is performed again.

On the other hand, as a result of the determination in step S308, when the imaging switch 144 is operated (YES in step S308), the processing proceeds to step S309.

In step S309, the image processing unit 150 (specifically, the reconstruction unit 151) obtains N pieces of the tomographic images (specifically, the original data pieces of the tomographic images) of the subject's eye E based on the image signals output from the line sensor 111 according to the control of the control unit 130.

Subsequently, in step S310, the image processing unit 150 (specifically, the reconstruction unit 151) averages the luminance of the N pieces of the tomographic images obtained in step S309 and generates one piece of the tomographic image. When the processing in step S310 is finished, the imaging is terminated, and the processing in the flowchart in FIG. 10 is terminated.

When the processing in step S304 is finished, when the processing in step S306 is finished, or when it is determined in step S307 that the luminance increasing operation unit 145 is operated (YES in step S307), the processing proceeds to step S201.

The processing in step S201 and subsequent steps illustrated in FIG. 10 is similar to the processing in step S201 and subsequent steps illustrated in FIG. 9, however, the processing is described below.

In step S201, for example, the control unit 130 (or the image processing unit 150) performs processing for setting the number of obtained tomographic images n to zero.

Subsequently, in step S202, for example, the control unit 130 (or the image processing unit 150) determines whether the number of obtained tomographic images n is less than the total number of obtained tomographic images Nm.

As a result of the determination in step S202, when the number of obtained tomographic images n is less than the total number of obtained tomographic images Nm (YES in step S202), the processing proceeds to step S203.

In step S203, for example, the control unit 130 (or the image processing unit 150) performs processing for incrementing the number of obtained tomographic images n by one.

When the processing in step S203 is finished, or when it is determined in step S202 that the number of obtained tomographic images n is not less than the total number of obtained tomographic images Nm (NO in step S202), the processing proceeds to step S204.

In step S204, the control unit 130 determines whether the optical path length operation unit 141 is operated.

As a result of the determination in step S204, when the optical path length operation unit 141 is operated (YES in step S204), the processing proceeds to step S205.

In step S205, for example, the control unit 130 (or the image processing unit 150) performs processing for setting the number of obtained tomographic images n to one.

Subsequently, in step S206, the optical path length control unit 131 in the control unit 130 controls the reflection mirror 106 to move by an amount corresponding to the operation amount of the optical path length operation unit 141.

When the processing in step S206 is finished, or when it is determined in step S204 that the optical path length operation unit 141 is not operated (NO in step S204), the processing proceeds to step S207.

In step S207, the control unit 130 determines whether the focus operation unit 143 is operated.

As a result of the determination in step S207, when the focus operation unit 143 is operated (YES in step S207), the processing proceeds to step S208.

In step S208, for example, the control unit 130 (or the image processing unit 150) performs the processing for setting the number of obtained tomographic images n to one.

Subsequently, in step S209, the focus lens control unit 133 in the control unit 130 controls the focus lens 121b to move by an amount corresponding to the operation amount of the focus operation unit 143.

When the processing in step S209 is finished, or when it is determined in step S207 that the focus operation unit 143 is not operated (NO in step S207), the processing proceeds to step S210.

In step S210, the control unit 130 determines whether the luminance increasing operation unit 145 is operated.

As a result of the determination in step S210, when the luminance increasing operation unit 145 is operated (YES in step S210), the processing proceeds to step S211.

In step S211, for example, the control unit 130 performs a setting to double the total number of obtained tomographic images Nm and halve the number of B-scan points.

When the processing in step S211 is finished, or when it is determined in step S210 that the luminance increasing operation unit 145 is not operated (NO in step S210), the processing proceeds to step S212.

In step S212, the control unit 130 determines whether the luminance decreasing operation unit 146 is operated.

As a result of the determination in step S212, when the luminance decreasing operation unit 146 is operated (YES in step S212), the processing proceeds to step S213.

In step S213, for example, the control unit 130 performs a setting to halve the total number of obtained tomographic images Nm and double the number of B-scan points.

When the processing in step S213 is finished, or when it is determined in step S212 that the luminance decreasing operation unit 146 is not operated (NO in step S212), the processing proceeds to step S214.

In step S214, the control unit 130 determines whether the imaging switch 144 is operated.

As a result of the determination in step S214, when the imaging switch 144 is not operated (NO in step S214), the processing proceeds to step S215.

In step S215, the image processing unit 150 (specifically, the reconstruction unit 151) obtains one piece of the tomographic image (specifically, the original data of the tomographic image) of the subject's eye E based on the image signal output from the line sensor 111 according to the control of the control unit 130. The image processing unit 150 (specifically, the reconstruction unit 151) which performs the processing for obtaining the tomographic image of the subject's eye E constitutes the obtainment unit.

Subsequently, in step S216, the image processing unit 150 (specifically, the reconstruction unit 151) performs processing for superimposing the latest n pieces of the tomographic images with each other and generating one piece of the tomographic image as a composite image. According to the present exemplary embodiment, the image processing unit 150 (specifically, the reconstruction unit 151) successively generates the composite images every time the processing in step S216 is repeatedly performed (specifically, every time one piece of the tomographic image is obtained in step S215). The image processing unit 150 (specifically, the reconstruction unit 151) which performs the processing for successively generating the composite images constitutes the generation unit.

Subsequently, in step S217, the image processing unit 150 (specifically, the enhancement processing unit 153) performs processing for multiplying the luminance of the tomographic image generated in step S216 by Nm/n. The image processing unit 150 (specifically, the enhancement processing unit 153) which performs the processing in step S217 constitutes the luminance change unit (the intensity change unit according to an aspect of the present invention).

Subsequently, in step S218, the control unit 130 performs control to display the tomographic image obtained by the processing in step S217 on the display unit 160. The control unit 130 which performs the control to display the tomographic image (the composite image) on the display unit 160 constitutes the display control unit. According to the present exemplary embodiment, considering that the second imaging mode is the mode for suitably capturing an image of the vitreous body region (the second region) of the subject's eye E, and the vitreous body region is drawn in high luminance, it is desirable that the tomographic image (the second tomographic image) of the composite image displayed in the present step is higher in the luminance than the tomographic image (the first tomographic image) displayed in step S103. Further, according to the present exemplary embodiment, the control unit 130 performs control to display a moving image of the tomographic images (the composite images) successively generated in step S216 and then successively subjected to the processing for changing the luminance in step S217 on the display unit 160. Subsequently, the processing returns to step S202, and the processing in step S202 and subsequent steps is performed again.

As a result of the determination in step S214, when the imaging switch 144 is operated (YES in step S214), the processing proceeds to step S219.

In step S219, the image processing unit 150 (specifically, the reconstruction unit 151) obtains N pieces of the tomographic images (specifically, the original data pieces of the tomographic images) of the subject's eye E based on the image signals output from the line sensor 111 according to the control of the control unit 130.

Subsequently, in step S220, the image processing unit 150 (specifically, the reconstruction unit 151) averages the luminance of the N pieces of the tomographic images obtained in step S219 and generates one piece of the tomographic image. When the processing in step S220 is finished, the imaging is terminated, and the processing in the flowchart in FIG. 10 is terminated.

According to the processing in the flowchart in FIG. 10, in step S216, the processing for generating the one piece of the tomographic image as the composite image is performed by superimposing the latest n pieces of the tomographic images with each other, however, the present exemplary embodiment is not limited to this aspect as with the processing in the flowchart in FIG. 9 according to the second exemplary embodiment. For example, the present exemplary embodiment can be applied to an aspect that the image processing unit 150 (specifically, the reconstruction unit 151) changes the number of tomographic images to be superimposed to generate the composite image. The image processing unit 150 (specifically, the reconstruction unit 151) which performs the processing for changing the number of tomographic images to be superimposed constitutes the number-of-pieces change unit, and the detailed processing for changing the number of tomographic images to be superimposed is similar to that in the above-described second exemplary embodiment, so that the descriptions thereof are omitted.

The ophthalmologic imaging apparatus 100 according to the third exemplary embodiment starts generation of the composite image (step S216 in FIG. 10) with at least any one of the movement of the reflection mirror 106 as the optical path length adjustment optical unit (step S304 in FIG. 10), the movement of the focus lens 121*b* as the focus adjustment optical unit (step S306 in FIG. 10), and the operation on the luminance increasing operation unit 145 (YES in step S307 in FIG. 10) as a trigger in the second imaging mode in addition to the processing according to the first exemplary embodiment and the second exemplary embodiment.

According to the above-described configuration, the tomographic image for observing the vitreous body region (the second region) of the subject's eye E is only generated when the detailed adjustment is performed, so that an excellent tomographic image can be obtained after performing suitable adjustment before imaging.

Other Embodiments

According to the above-described first to third exemplary embodiments, it is described that the imaging mode switching operation unit 147 has the first imaging mode and the second imaging mode as the switchable imaging modes, however, the present invention is not limited to this configuration. For example, the present invention can be applied to a configuration in which the imaging mode switching operation unit 147 has another imaging mode as the switchable imaging modes thereof in addition to the first imaging mode and the second imaging mode. In this configuration, the imaging mode switching operation unit 147 can switch to the imaging mode other than the first imaging mode and the second imaging mode.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-076838, filed Apr. 6, 2016, which is hereby incorporated by reference herein in its entirety.

What is claimed is:

1. An ophthalmologic imaging apparatus which captures a tomographic image of a subject's eye using interference light obtained by combining a return light from the subject's eye irradiated by measurement light and a reference light, the ophthalmologic imaging apparatus comprising:
    a selection unit configured to select any of a plurality of imaging modes including a first imaging mode for obtaining a first tomographic image of a retina region and a vitreous body region of the subject's eye and a second imaging mode, which is different from the first imaging mode, for obtaining a second tomographic image of the vitreous body region more suitable than that in the first tomographic image; and
    a control unit configured to perform (a) control, in a case that the first imaging mode is selected, to display the first tomographic image on a display unit and (b) control, in a case that the second imaging mode is selected, to display the second tomographic image on the display unit.

2. The ophthalmologic imaging apparatus according to claim 1, further comprising:
    a generation unit configured to successively generate composite images by superimposing a plurality of tomographic images successively obtained in the case that the second imaging mode is selected,
    wherein the control unit performs (a) control, in the case that the first imaging mode is selected, to display tomographic images of the subject's eye successively obtained as first tomographic images on the display unit and (b) control, in the case that the second imaging mode is selected, to display the composite images successively generated as second tomographic images on the display unit.

3. The ophthalmologic imaging apparatus according to claim 2 further comprising a number-of-pieces change unit configured to change a number of tomographic images to be superimposed with each other in the case that the composite image is generated.

4. The ophthalmologic imaging apparatus according to claim 3, wherein the number-of-pieces change unit changes the number of tomographic images to be superimposed with each other according to intensity of the composite image.

5. The ophthalmologic imaging apparatus according to claim 3, wherein
    the number-of-pieces change unit changes the number of tomographic images to be superimposed with each other according to intensity of the vitreous body region in the composite image.

6. The ophthalmologic imaging apparatus according to claim 2, further comprising:
    an optical path length adjustment optical unit configured to adjust an optical path length of the reference light;
    a focus adjustment optical unit configured to adjust a focus of the measurement light; and
    an intensity increasing operation unit configured to increase intensity of the tomographic image of the subject's eye as a trigger in the second imaging mode,
    wherein the generation unit starts generation of the composite image with at least any one of movement of the optical path length adjustment optical unit, movement of the focus adjustment optical unit, and an operation on the intensity increasing operation unit.

7. The ophthalmologic imaging apparatus according to claim 2, wherein
    in the case that the second imaging mode is selected, the generation unit successively generates the composite images as the second tomographic images so that intensity thereof is higher than that of the first tomographic image.

8. The ophthalmologic imaging apparatus according to claim 2, wherein
the generation unit sets an area to be a reference of position adjustment before performing superimposition of tomographic images of the subject's eye closer to a coherence gate side in the case that the second imaging mode is selected than the case that the first imaging mode is selected, and, in the case that the second imaging mode is selected, the generation unit adjusts positions of the plurality of the tomographic images based on the set area and successively generates the composite images by superimposing the plurality of the tomographic images subjected to the position adjustment with each other.

9. The ophthalmologic imaging apparatus according to claim 1, further comprising:
an optical path length adjustment optical unit configured to adjust an optical path length of the reference light,
wherein the control unit controls the optical path length adjustment optical unit to move so that an optical path length of the reference light is shorter in the case that the second imaging mode is selected than the case that the first imaging mode is selected.

10. The ophthalmologic imaging apparatus according to claim 1,
further comprising a focus adjustment optical unit configured to adjust a focus of the measurement light, and
wherein the control unit controls the focus adjustment optical unit to move so that a focus position of the measurement light is closer to the ophthalmologic imaging apparatus in the case that the second imaging mode is selected than the case that the first imaging mode is selected.

11. The ophthalmologic imaging apparatus according to claim 1, further comprising:
an intensity change unit configured to change intensity of a tomographic image of the subject's eye, and
wherein the control unit performs (a) control, in the case that the first imaging mode is selected, to display the tomographic image of which intensity is not changed as the first tomographic image on the display unit and (b) control, in the case that the second imaging mode is selected, to display a tomographic image of which intensity is increased as the second tomographic image on the display unit.

12. The ophthalmologic imaging apparatus according to claim 1, wherein, in a case that a tomographic image captured according to the selected imaging mode is displayed on the display unit, the control unit performs control to move an adjustment optical unit included in the ophthalmologic imaging apparatus according to the selected imaging mode.

13. The ophthalmologic imaging apparatus according to claim 1, wherein the control unit performs (a) control, in the case that the first imaging mode is selected, to display the first tomographic image as a moving image on the display unit and (b) control, in the case that the second imaging mode is selected, to display the second tomographic image as a moving image on the display unit.

14. A method for controlling an ophthalmologic imaging apparatus which captures a tomographic image of a subject's eye using interference light obtained by combining a return light from the subject's eye irradiated by measurement light and a reference light, the method comprising:
selecting any of a plurality of imaging modes including a first imaging mode for obtaining a first tomographic image of a retina region and a vitreous body region of the subject's eye and a second imaging mode, which is different from the first imaging mode, for obtaining a second tomographic image of the vitreous body region more suitable than that in the first tomographic image; and
performing (a) control, in a case that the first imaging mode is selected, to display the first tomographic image on a display unit and (b) control, in a case that the second imaging mode is selected, to display the second tomographic image of the subject's eye on the display unit.

15. A non-transitory computer readable storage medium storing a program that when executed by a computer causes the computer to perform a method of controlling an ophthalmologic imaging apparatus, the ophthalmologic imaging apparatus capturing a tomographic image of a subject's eye using interference light obtained by combining a return light from the subject's eye irradiated by measurement light and a reference light, the method comprising:
selecting any of a plurality of imaging modes including a first imaging mode for obtaining a first tomographic image of a retina region and a vitreous body region of the subject's eye and a second imaging mode, which is different from the first imaging mode, for obtaining a second tomographic image of the vitreous body region more suitable than that in the first tomographic image; and
performing (a) control, in a case that the first imaging mode is selected, to display the first tomographic image on a display unit and (b) control, in a case that the second imaging mode is selected, to display the second tomographic image on the display unit.

16. The ophthalmologic imaging apparatus according to claim 1, further comprising a generation unit configured to generate the second tomographic image so that intensity of the second tomographic image become higher than that of the first tomographic image.

* * * * *